(12) United States Patent
Krulevitch et al.

(10) Patent No.: US 9,724,475 B2
(45) Date of Patent: Aug. 8, 2017

(54) DRUG DELIVERY MANAGEMENT SYSTEMS AND METHODS

(75) Inventors: Peter Krulevitch, Pleasanton, CA (US); Ulrich Kraft, Hofheim (DE); Robert Wilk, Sierra Village, CA (US); Zara Sieh, San Ramon, CA (US); Mitch Zhao, San Jose, CA (US)

(73) Assignee: LifeScan, Inc., Wayne, PA (US)

( * ) Notice: Subject to any disclaimer, the term of this patent is extended or adjusted under 35 U.S.C. 154(b) by 1201 days.

(21) Appl. No.: 13/203,707

(22) PCT Filed: Jan. 27, 2010

(86) PCT No.: PCT/US2010/022245
§ 371 (c)(1),
(2), (4) Date: Sep. 8, 2011

(87) PCT Pub. No.: WO2010/098931
PCT Pub. Date: Sep. 2, 2010

(65) Prior Publication Data
US 2011/0313395 A1    Dec. 22, 2011

Related U.S. Application Data

(60) Provisional application No. 61/156,386, filed on Feb. 27, 2009, provisional application No. 61/156,421,
(Continued)

(51) Int. Cl.
*A61M 5/315* (2006.01)
*A61M 5/24* (2006.01)
(Continued)

(52) U.S. Cl.
CPC .............. *A61M 5/315* (2013.01); *A61M 5/24* (2013.01); *A61M 5/3129* (2013.01);
(Continued)

(58) Field of Classification Search
CPC ...... A61M 5/31525; A61M 2005/3142; A61M 5/31551; A61M 2205/3317;
(Continued)

(56) References Cited

U.S. PATENT DOCUMENTS 4,803,625 A   2/1989  Fu et al.
4,950,246 A   8/1990  Muller
(Continued)

FOREIGN PATENT DOCUMENTS

CA    2126934 A1    12/1994
CA    2126934 C     10/2005
(Continued)

OTHER PUBLICATIONS

Chinese Patent Application No. 201080019326.9, Chinese First Office Action dated Feb. 6, 2013, 6 pages, State Intellectual Property Office, P.R. China.
(Continued)

*Primary Examiner* — Bhisma Mehta
*Assistant Examiner* — Hamza Darb

(57) ABSTRACT

Various embodiments of a "smart" drug delivery pen are provided which include a drug delivery pen having an inertial sensor or accelerometer. A system is also provided that includes the smart drug pen in conjunction with a data management unit(s) DMU. Various exemplary methods for use of the pens and systems are also described and illustrated.

19 Claims, 11 Drawing Sheets

Related U.S. Application Data filed on Feb. 27, 2009, provisional application No. 61/156,472, filed on Feb. 27, 2009, provisional application No. 61/164,250, filed on Mar. 27, 2009.

(51) Int. Cl.
*A61M 5/31* (2006.01)
*G06F 19/00* (2011.01)
*A61B 5/145* (2006.01)
*G01D 5/165* (2006.01)
*A61B 5/00* (2006.01)

(52) U.S. Cl.
CPC ..... *A61M 5/31525* (2013.01); *G06F 19/3468* (2013.01); *A61B 5/002* (2013.01); *A61B 5/14532* (2013.01); *A61M 5/3146* (2013.01); *A61M 5/31551* (2013.01); *A61M 2005/3126* (2013.01); *A61M 2005/3142* (2013.01); *A61M 2205/14* (2013.01); *A61M 2205/18* (2013.01); *A61M 2205/215* (2013.01); *A61M 2205/3317* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/52* (2013.01); *A61M 2205/581* (2013.01); *A61M 2205/583* (2013.01); *A61M 2205/584* (2013.01); *A61M 2205/6054* (2013.01); *A61M 2205/6081* (2013.01); *A61M 2205/8212* (2013.01); *A61M 2209/04* (2013.01); *G01D 5/1655* (2013.01)

(58) Field of Classification Search
CPC .. A61M 2205/3592; A61M 2205/3561; A61M 2205/6081; A61M 2205/583; A61M 2205/581; A61M 2205/584; A61M 2205/3553; A61M 2205/3569
USPC .................................................. 604/207–211
See application file for complete search history.

(56) References Cited

U.S. PATENT DOCUMENTS

| | | | |
|---|---|---|---|
| 4,995,402 A | 2/1991 | Smith et al. | |
| 5,204,670 A | 4/1993 | Stinton | |
| 5,216,597 A | 6/1993 | Beckers | |
| 5,383,865 A | 1/1995 | Michael | |
| 5,417,222 A | 5/1995 | Dempsey et al. | |
| 5,536,249 A * | 7/1996 | Castellano et al. | 604/65 |
| 5,558,638 A | 9/1996 | Evers et al. | |
| 5,593,390 A | 1/1997 | Castellano et al. | |
| 5,611,784 A | 3/1997 | Barresi et al. | |
| 5,678,562 A | 10/1997 | Sellers | |
| 5,728,074 A | 3/1998 | Castellano et al. | |
| 5,820,602 A * | 10/1998 | Kovelman et al. | 604/187 |
| 5,830,152 A | 11/1998 | Tao | |
| 5,925,021 A | 7/1999 | Castellano et al. | |
| 5,950,632 A | 9/1999 | Reber et al. | |
| 5,957,896 A | 9/1999 | Bendek et al. | |
| 6,024,699 A | 2/2000 | Surwit et al. | |
| 6,038,676 A | 3/2000 | Yanes et al. | |
| 6,134,504 A | 10/2000 | Douglas et al. | |
| 6,144,922 A | 11/2000 | Douglas et al. | |
| 6,192,891 B1 | 2/2001 | Gravel et al. | |
| 6,235,004 B1 | 5/2001 | Steenfeldt-Jensen et al. | |
| 6,270,455 B1 | 8/2001 | Brown | |
| 6,277,099 B1 | 8/2001 | Strowe et al. | |
| 6,287,283 B1 | 9/2001 | Ljunggreen et al. | |
| 6,298,017 B1 | 10/2001 | Kulakowski et al. | |
| 6,443,890 B1 | 9/2002 | Schulze et al. | |
| 6,482,185 B1 | 11/2002 | Hartmann | |
| 6,524,239 B1 | 2/2003 | Reed et al. | |
| 6,540,672 B1 | 4/2003 | Simonsen et al. | |
| 6,554,798 B1 | 4/2003 | Mann et al. | |
| 6,585,698 B1 | 7/2003 | Packman et al. | |
| 6,641,533 B2 | 11/2003 | Causey, III et al. | |
| 6,663,602 B2 | 12/2003 | Moller | |
| 6,790,178 B1 | 9/2004 | Mault et al. | |
| 6,817,986 B2 | 11/2004 | Slate et al. | |
| 6,869,413 B2 * | 3/2005 | Langley et al. | 604/65 |
| 6,942,646 B2 | 9/2005 | Langley et al. | |
| 7,169,132 B2 | 1/2007 | Bendek et al. | |
| 7,397,730 B2 | 7/2008 | Skyggebjerg et al. | |
| 7,427,275 B2 | 9/2008 | DeRuntz et al. | |
| 7,713,229 B2 | 5/2010 | Veit et al. | |
| 2002/0010432 A1 * | 1/2002 | Klitmose | 604/232 |
| 2002/0052578 A1 | 5/2002 | Moller | |
| 2002/0126036 A1 | 9/2002 | Flaherty et al. | |
| 2003/0005891 A1 | 1/2003 | Lu | |
| 2003/0023203 A1 | 1/2003 | Lavi et al. | |
| 2003/0038047 A1 | 2/2003 | Sleva et al. | |
| 2003/0208113 A1 | 11/2003 | Mault et al. | |
| 2003/0220814 A1 | 11/2003 | Gordon | |
| 2003/0233069 A1 | 12/2003 | Gillespie, Jr. et al. | |
| 2004/0024364 A1 | 2/2004 | Langley et al. | |
| 2004/0051368 A1 | 3/2004 | Caputo et al. | |
| 2004/0122355 A1 | 6/2004 | Langley et al. | |
| 2005/0049179 A1 | 3/2005 | Davidson et al. | |
| 2005/0090781 A1 | 4/2005 | Baba et al. | |
| 2005/0177398 A1 | 8/2005 | Watanabe et al. | |
| 2005/0182358 A1 * | 8/2005 | Veit et al. | 604/93.01 |
| 2006/0153693 A1 | 7/2006 | Fiechter et al. | |
| 2006/0173260 A1 | 8/2006 | Gaoni et al. | |
| 2006/0224123 A1 | 10/2006 | Friedli et al. | |
| 2007/0021715 A1 | 1/2007 | Kohlbrenner et al. | |
| 2007/0060796 A1 | 3/2007 | Kim | |
| 2007/0060800 A1 | 3/2007 | Drinan et al. | |
| 2007/0123829 A1 | 5/2007 | Atterbury et al. | |
| 2007/0129708 A1 | 6/2007 | Edwards et al. | |
| 2007/0219503 A1 | 9/2007 | Loop et al. | |
| 2008/0099366 A1 | 5/2008 | Niemiec et al. | |
| 2008/0125713 A1 | 5/2008 | Nemoto et al. | |
| 2008/0147044 A1 * | 6/2008 | Palmer et al. | 604/514 |
| 2008/0188813 A1 | 8/2008 | Miller et al. | |
| 2008/0208142 A1 | 8/2008 | Moller | |
| 2008/0287883 A1 | 11/2008 | Radmer et al. | |
| 2008/0306434 A1 | 12/2008 | Dobbles et al. | |
| 2008/0312605 A1 | 12/2008 | Saiki | |
| 2009/0012479 A1 | 1/2009 | Moller et al. | |
| 2009/0163793 A1 | 6/2009 | Koehler et al. | |
| 2010/0286665 A1 | 11/2010 | Manna et al. | |
| 2010/0292635 A1 | 11/2010 | Sundar | |
| 2011/0028906 A1 | 2/2011 | Baba et al. | |
| 2011/0306927 A1 | 12/2011 | Watanabe et al. | |

FOREIGN PATENT DOCUMENTS

| | | |
|---|---|---|
| CA | 2644547 A1 | 11/2007 |
| CN | 1602212 A | 3/2005 |
| CN | 1871046 A | 11/2006 |
| CN | 1871783 A | 11/2006 |
| CN | 101068586 A | 11/2007 |
| EP | 0777123 A2 | 6/1997 |
| EP | 1363224 A1 | 11/2003 |
| EP | 1462134 A1 | 9/2004 |
| JP | S6244505 A | 2/1987 |
| JP | H067741 U | 2/1994 |
| JP | 2000237309 A | 9/2000 |
| JP | 2001017542 A | 1/2001 |
| JP | 2001087386 A | 4/2001 |
| JP | 2001170176 A | 6/2001 |
| JP | 2004000555 A | 1/2004 |
| JP | 2004024699 A | 1/2004 |
| JP | 2004164564 A | 6/2004 |
| JP | 2004516111 A | 6/2004 |
| JP | 2007506470 A | 3/2007 |
| JP | 2007510469 A | 4/2007 |
| JP | 2007313374 A | 12/2007 |
| JP | 2008531151 A | 8/2008 |
| WO | 9902210 A1 | 1/1999 |
| WO | WO 99/043283 A1 | 9/1999 |

(56) References Cited

FOREIGN PATENT DOCUMENTS

| WO | 02051480 A1 | 7/2002 |
|---|---|---|
| WO | WO 02/062212 A3 | 8/2002 |
| WO | WO 03/005891 A1 | 1/2003 |
| WO | WO 03/047426 A1 | 6/2003 |
| WO | 2004006785 A1 | 1/2004 |
| WO | WO 2004/006785 A1 | 1/2004 |
| WO | 2006051856 A1 | 5/2006 |
| WO | WO 2006/075016 A1 | 7/2006 |
| WO | 2006109779 A1 | 10/2006 |
| WO | 2009024562 A1 | 2/2009 |
| WO | 2009083600 A1 | 7/2009 |
| WO | 2010100883 A1 | 9/2010 |

OTHER PUBLICATIONS

European Patent Application No. 10746603.9, extended European search report dated Jan. 10, 2013, 8 pages, European Patent Office, Germany.
First Office Action issued in related Chinese Patent Application No. 201080019324.X, issued May 24, 2013, 19 pages.
Second Office Action issued in related Chinese Patent Application No. 201080019324.X, issued Dec. 12, 2013, 22 pages.
Search Report issued in related Chinese Patent Application No. 201080019324.X, dated May 17, 2013, 2 pages.
First Office Action issued in related Chinese Patent Application No. 201080019326.9, issued Feb. 6, 2013, 12 pages.
Second Office Action issued in related Chinese Patent Application No. 201080019326.9, issued Jul. 30, 2013, 12 pages.
Third Office Action issued in related Chinese Patent Application No. 201080019326.9, issued Dec. 27, 2013, 11 pages.
Fourth Office Action issued in related Chinese Patent Application No. 201080019326.9, issued Jul. 16, 2014, 20 pages.
Search Report issued in related Chinese Patent Application No. 201080019326.9, dated Jan. 29, 2013, 2 pages.
Search Report issued in related Chinese Patent Application No. 201080019326.9, dated Jul. 23, 2013, 2 pages.
Search Report issued in related Chinese Patent Application No. 201080019326.9, dated Jul. 8, 2014, 2 pages.
First Office Action issued in related Chinese Patent Application No. 201080019285.3, issued Feb. 5, 2013, 9 pages.
Second Office Action issued in related Chinese Patent Application No. 201080019285.3, issued Oct. 12, 2013, 6 pages.
Search Report issued in related Chinese Patent Application No. 201080019285.3, dated Jan. 28, 2013, 2 pages.
Partial European Search Report issued in related European Patent Application No. 14168182.5, dated Jul. 7, 2014, 14 pages.
Notice of Reasons for Rejection issued in related Japanese Patent Application No. 2011-552048, transmitted Dec. 17, 2013, 10 pages.
Notice of Reasons for Rejection issued in related Japanese Patent Application No. 2011-552048, transmitted Jun. 24 2014, 4 pages.
Notice of Reasons for Rejection issued in related Japanese Patent Application No. 2011-552049, transmitted Dec. 17, 2013, 11 pages.
Notice of Reasons for Rejection issued in related Japanese Patent Application No. 2011-552049, transmitted Jun. 24, 2014, 4 pages.
Notice of Reasons for Rejection issued in related Japanese Patent Application No. 2011-552050, transmitted Dec. 17, 2013, 8 pages.
Notice of Reasons for Rejection issued in related Japanese Patent Application No. 2011-552050, transmitted Jun. 24, 2014, 7 pages.
Notice of Reasons for Rejection issued in related Japanese Patent Application No. 2011-552051, transmitted Dec. 17, 2013, 9 pages.
Notice of Reasons for Rejection issued in related Japanese Patent Application No. 2011-552051, transmitted Jun. 24, 2014, 4 pages.
International Preliminary Report on Patentability issued in related International Patent Application No. PCT/US2010/022236, issued Aug. 30, 2011, 9 pages.
International Search Report issued in related International Patent Application No. PCT/US2010/022236, mailed Mar. 23, 2010, 4 pages.
Written Opinion issued in related International Patent Application No. PCT/US2010/022236, mailed Mar. 23, 2010, 10 pages.
International Preliminary Report on Patentability issued in related International Patent Application No. PCT/US2010/022241, issued Aug. 30, 2011, 9 pages.
International Search Report issued in related International Patent Application No. PCT/US2010/022241, mailed Mar. 23, 2010, 4 pages.
Written Opinion issued in related International Patent Application No. PCT/US2010/022241, mailed Mar. 23, 2010, 10 pages.
International Preliminary Report on Patentability issued in related International Patent Application No. PCT/US2010/022242, issued Aug. 30, 2011, 7 pages.
International Search Report issued in related International Patent Application No. PCT/US2010/022242, mailed Mar. 12, 2010, 4 pages.
Written Opinion issued in related International Patent Application No. PCT/US2010/022242, mailed Mar. 12, 2010, 8 pages.
International Preliminary Report on Patentability issued in related International Patent Application No. PCT/US2010/022245, issued Aug. 30, 2011, 9 pages.
International Search Report issued in related International Patent Application No. PCT/US2010/022245, mailed Mar. 23, 2010, 4 pages.
Written Opinion issued in related International Patent Application No. PCT/US2010/022245, mailed Mar. 23, 2010, 10 pages.
Second Office Action issued in related Chinese Patent Application No. 201080019286.8, issued Jun. 24, 2013, 9 pages.
Third Office Action issued in related Chinese Patent Application No. 201080019286.8, issued Sep. 29, 2013, 8 pages.
European Search Report issued in related European Patent Application No. 10746603.9, dated Jan. 10, 2013, 8 pages.
Supplemental European Search Report issued in related European Patent Application No. 10746603.9, dated Jul. 5, 2013, 4 pages.
First Office Action issued in related Chinese Patent Application No. 201080019286.8, issued Dec. 5, 2012, 23 pages.
Search Report issued in related Chinese Patent Application No. 201080019286.8, dated Nov. 26, 2012, 2 pages.
M. Franetzki, et al., "Design and Data of a Compact Device for Sustained Program-Controlled Medicament Infusion" Hormone and Metabolic Research, Supplement Series (1982), 12 (Islet-Pancreas-Transplant. Artif. Pancreas), 169-172, ISSN: 0170-5903, ISBN: 086577062x.
Lord, et al., "MiniMed Technologies Programmable Implantable Infusion Systyem," Annals of the New York Academy of Sciences, 1988;531:66-71.
Prestele, et al., "A Remote-Programmable Implantable Insulin Dosing Device Part 1" Techincal Concept and Features, Hormone and Metabolic Research, Supplement Series (1982), 12 (Islet-Pancreas-Transplant. Artif. Pancreas), 304-7, ISSN: 0170-5903, ISBN: 086577062x.
Christopher D. Saudek, "Development of Implantable Insulin Infusion Devices", Methods in Diabetes Research, vol. II: Clinical Methods, 1986, pp. 347-360, Editors Clarke, William; Lamer, Joseph; et al.
HumaPen Memoir (revised Nov. 20, 2006) (retrieved from http://pi.lilly.com/us/memoir_user_manual.pdf accessed on Mar. 15, 2010).
The Smart Pen by John Walsh, May 18, 2008 (retrieved from http://challengediabetes.diabetech.net/2008/05/14the-smart-insu-lin-pen-by-john-walsh/ accessed on Mar. 15, 2010.
The Smart Pen by John Walsh, (retrieved from http://www.diabetesnet.com/diabetes_technology/smart_pen.php accessed on Mar. 15, 2010).
European Search Report issued in related European Patent Application No. 14168182.5, dated Dec. 1, 2014, 18 pages.
First Office Action issued in related Chinese Patent Application No. 201310512273.X, dated Jan. 6, 2015, 16 pages.
Decision on Rejection issued in related Chinese Patent Application No. 201080019326.9, dated Jan. 9, 2015, 11 pages.
Supplementary European Search Report issued in related European Patent Application No. 10746600, dated May 6, 2015, 14 pages.

(56) References Cited

OTHER PUBLICATIONS

Supplementary European Search Report issued in related European Patent Application No. 10746601, dated May 6, 2015, 14 pages.
Supplementary European Search Report issued in related European Patent Application No. 10746602, dated May 6, 2015, 13 pages.
European Search Report issued in related European Patent Application No. 15164132, dated Aug. 28, 2015, 13 pages.
Office Action issued in corresponding Canadian Application No. 2,753,138, mailed Apr. 5, 2016, 6 pages.
Office Action issued in corresponding Canadian Application No. 2,753,069, mailed May 13, 2016, 8 pages.
Office Action issued in corresponding Canadian Application No. 2,753,139, mailed Apr. 26, 2016, 6 pages.
Office Action issued in corresponding Canadian Application No. 2,753,140, mailed Apr. 26, 2016, 6 pages.

* cited by examiner

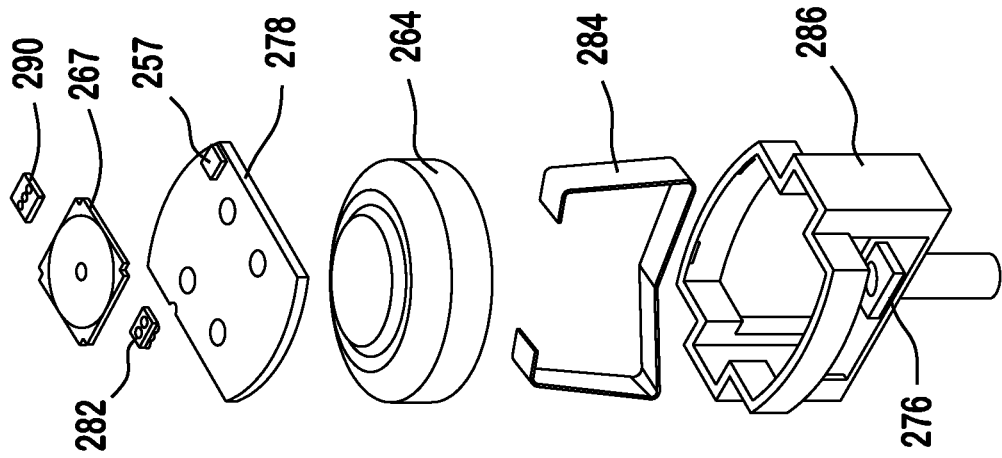
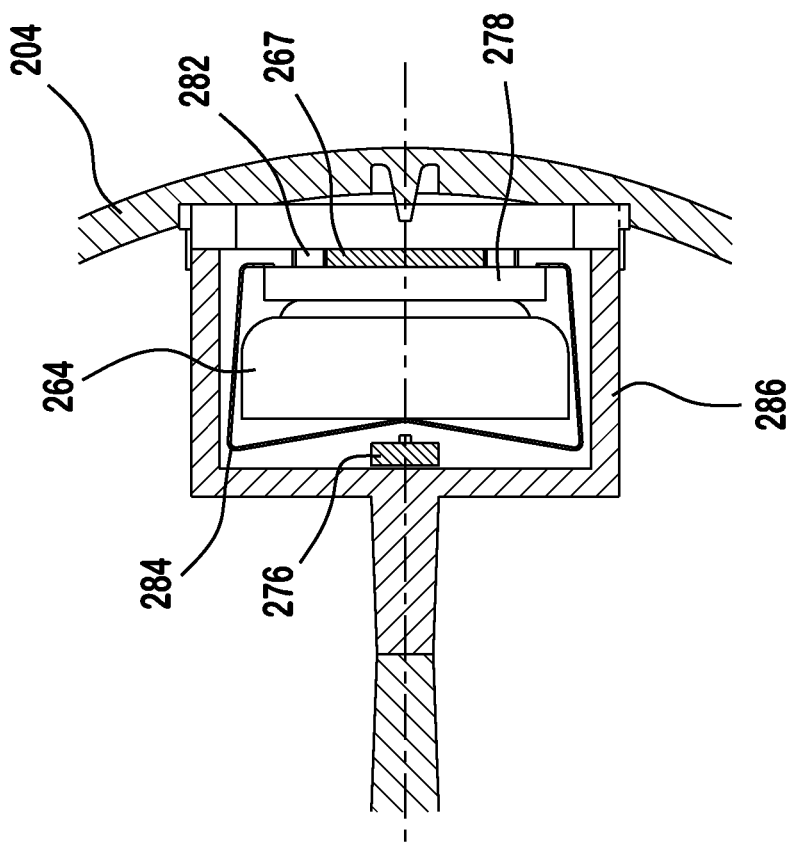
FIG. 8
FIG. 7

US 9,724,475 B2

DRUG DELIVERY MANAGEMENT SYSTEMS AND METHODS

PRIORITY

This application claims the benefits of priority under 35 USC§§120 and 371 of International Applications: (a) PCT/US2010/022236, filed Jan. 27, 2010 (which claims the benefit of priority under 35 USC§119 to Provisional Patent Application Ser. No. 61/156,386, filed on Feb. 27, 2009, entitled "Medical Module for Drug Delivery Pen"; (b) PCT/US2010/022241, filed Jan. 27, 2010 (which claims the benefit of priority under 35 USC§119 to Provisional Patent Application Ser. No. 61/156,421, filed on Feb. 27, 2009, entitled "Drug Delivery System"; (c) PCT/US2010/022242, filed Jan. 27, 2010 (which claims the benefit of priority under 35 USC§119 to Provisional Patent Application Ser. No. 61/156,472 filed on Feb. 27, 2009, entitled "Drug Delivery Management Systems and Methods"; (d) PCT/US2010/022245, filed Jan. 27, 2010 (which claims the benefit of priority under 35 USC§119 to Provisional Patent Application Ser. No. 61/164,250 filed on Mar. 27, 2009, entitled "DRUG DELIVERY MANAGEMENT SYSTEMS AND METHODS", all of the listed prior applications are hereby incorporated by reference in their entirety herein.

BACKGROUND

It is believed that five million people worldwide, or approximately 56% of all insulin users, use insulin pens to inject their insulin. Insulin pens are convenient, easy to use, and discrete compared to syringes and vials, resulting in improved adherence and better outcomes. In addition, insulin pens reduce the time required for health care practitioners to initiate insulin therapy.

SUMMARY OF THE DISCLOSURE

Embodiments of the present invention address key issues, including: bringing together insulin therapy and blood glucose monitoring into more integrated therapeutic/monitoring systems; simplifying insulin initiation and intensification protocols; making blood glucose values central in the management of diabetes; and providing diabetes system solutions for improved outcomes and lower costs. The embodiments of the present invention help the patient and care provider stay on top of insulin therapy by automatically communicating delivered doses to a data management unit, by recording the amount and time of insulin delivery, and by displaying a summary of a patient's blood glucose and insulin administration history. The embodiments of the present invention confirm whether the patient has already dosed, keeps track of the time and amount of insulin delivery, and eliminates the need to keep a manual logbook. Embodiments of the present invention help health care practitioners keep track of patient compliance.

Not only will embodiments of the invention facilitate management of diabetes, the invention and its embodiments will also be applicable in any field where drug delivery to a patient is utilized. For example, in the field of pain management or arthritis management, anxiety or epilepsy management (e.g., Diazepam) and the like.

In view of the foregoing and in accordance with one aspect of the present invention, there is provided a drug delivery pen. The drug delivery pen includes a pen housing, a microprocessor and an inertial sensor or accelerometer. The pen housing extends from a first end to a second end along a longitudinal axis. The housing encloses at least a portion of a plunger rod coupled to a drug cartridge disposed proximate one of the first and second ends. The drug cartridge includes a volume of one or more drugs disposed therein. The microprocessor is disposed in the housing and operatively connected to a power source and memory. The inertial sensor is connected to the housing and in electronic communication with the microprocessor so that the microprocessor is able to determine from output signals of the inertial sensor as to whether the housing has been shaken back and forth a predetermined number of times along the longitudinal axis to mix the one or more drugs disposed in the cartridge or whether the housing including the drug cartridge is oriented in a topmost position generally vertically with respect to the ground in a priming position.

In yet another aspect, a drug delivery pen is provided that includes a housing, drug cartridge, plunger rod, dosage selector, microprocessor and a momentary switch. The pen housing extends from a first end to a second end along a longitudinal axis. The housing is coupled to the drug cartridge disposed proximate one of the first and second ends. The drug cartridge includes a volume of one or more drugs disposed therein. The plunger rod has a portion disposed in the housing and at least a portion of the plunger rod coupled to the drug cartridge. The dosage selector is mounted to the housing and coupled to the plunger rod. The microprocessor is disposed in the housing and operatively connected to a power source and memory. The momentary switch is coupled to the plunger rod and electrically connected to the microprocessor so that actuation of the plunger rod to deliver drug causes the switch to be actuated and allows the microprocessor to detect actuation of the plunger.

In a further aspect, a diabetes management system is provided that includes a data management unit and a drug delivery pen. The data management unit includes a memory, processor, display, and transceiver. The drug delivery pen includes a pen housing, drug cartridge, a memory, processor, and an inertial sensor. The pen housing extends from a first end to a second end along a longitudinal axis. The housing is coupled to the drug cartridge disposed proximate one of the first and second ends. The processor is coupled to the memory. The inertial sensor is connected to the housing and in communication with the processor to allow for determination of the housing including the drug cartridge being oriented in a topmost position generally vertically with respect to the ground in a priming position or the housing being shaken back and forth along the longitudinal axis.

In another aspect, a drug delivery pen is provided that includes a pen housing, drug cartridge, microprocessor, and a radio-frequency-identification tag. The pen housing extends from a first end to a second end along a longitudinal axis. The housing is coupled to the drug cartridge disposed proximate one of the first and second ends. The drug cartridge includes a volume of one or more drugs disposed therein. The microprocessor is disposed in the housing and operatively connected to a power source and memory. The Radio-Frequency-Identification tag is coupled to the drug cartridge and configured to store information selected from a group including type of drug(s) in the cartridge, volume of drug in the cartridge, expiration date, batch date, lot number, manufacturer identification or combinations thereof.

In a further aspect, a diabetes management system is provided that includes a data management unit and a drug delivery pen. The data management unit includes a memory; processor coupled to the memory; a display coupled to the processor; a transceiver to receive and transmit data; and a radio-frequency-identification reader. The drug delivery pen includes a pen housing, drug cartridge, memory, processor, and RFID tag. The housing extends from a first end to a second end along a longitudinal axis, the housing being coupled to a drug cartridge disposed proximate one of the first and second ends. The pen housing has a dosage indicator window and a dosage selector coupled to the plunger rod. The processor is coupled to the memory. The radio-frequency-identification tag is attached to the drug cartridge and configured to store data selected from a group including a type of drug(s) in the cartridge, volume of drug in the cartridge, expiration date, batch date, lot number, manufacturer identification or combinations thereof.

In yet another aspect, a method of managing diabetes of a user with a glucose meter and a drug delivery pen is provided. The glucose meter has a microprocessor, memory, display and a wireless transceiver of data. The delivery pen has a pen housing that extends from a first end to a second end, the first end of the housing enclosing a plunger coupled to a drug cartridge disposed proximate the second end of the housing. The first end of the pen housing has a dosage indicator window and a dosage selector coupled to the plunger. The pen further includes a processing unit and a transceiver disposed in the housing. The method can be achieved by: loading a therapeutic administration protocol based on therapeutic requirements of the user into controller of the glucose meter in which the administration protocol includes protocol information specific to at least a drug type, dosage, and schedule for administration of the drug with the dosage based on at least glucose level of a user; storing in the controller of the glucose meter a plurality of measured glucose level in the user's biological fluid; displaying a recommended drug dosage based on the plurality of measured blood glucose level; determining whether the drug delivery pen has been primed; delivering the recommended dosage of a drug to a user via activation of the plunger with respect to the drug cartridge; measuring the actual dosage of the drug being delivered to the user; and storing data related to the actual dosage of the drug with a memory of the communication module; transmitting the data to the glucose meter via the transceiver of the communication module; and displaying information indicative of compliance to the therapeutic administration protocol.

These and other embodiments, features and advantages will become apparent when taken with reference to the following more detailed description of the embodiments of the invention in conjunction with the accompanying drawings that are first briefly described.

BRIEF DESCRIPTION OF THE FIGURES

The accompanying drawings, which are incorporated herein and constitute part of this specification, illustrate presently preferred exemplary embodiments of the invention, and, together with the general description given above and the detailed description given below, serve to explain features of the invention (wherein like numerals represent like elements), of which:

FIG. 7 illustrates a cross-sectional view of an electronic assembly of the drug delivery pen of FIG. 6, according to an exemplary embodiment described and illustrated herein.

FIG. 8 illustrates a perspective view of the electronic assembly of the drug delivery pen of FIG. 6, according to an exemplary embodiment described and illustrated herein.

DETAILED DESCRIPTION OF THE FIGURES

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

First Type of Drug Delivery Pen

Figure 1:
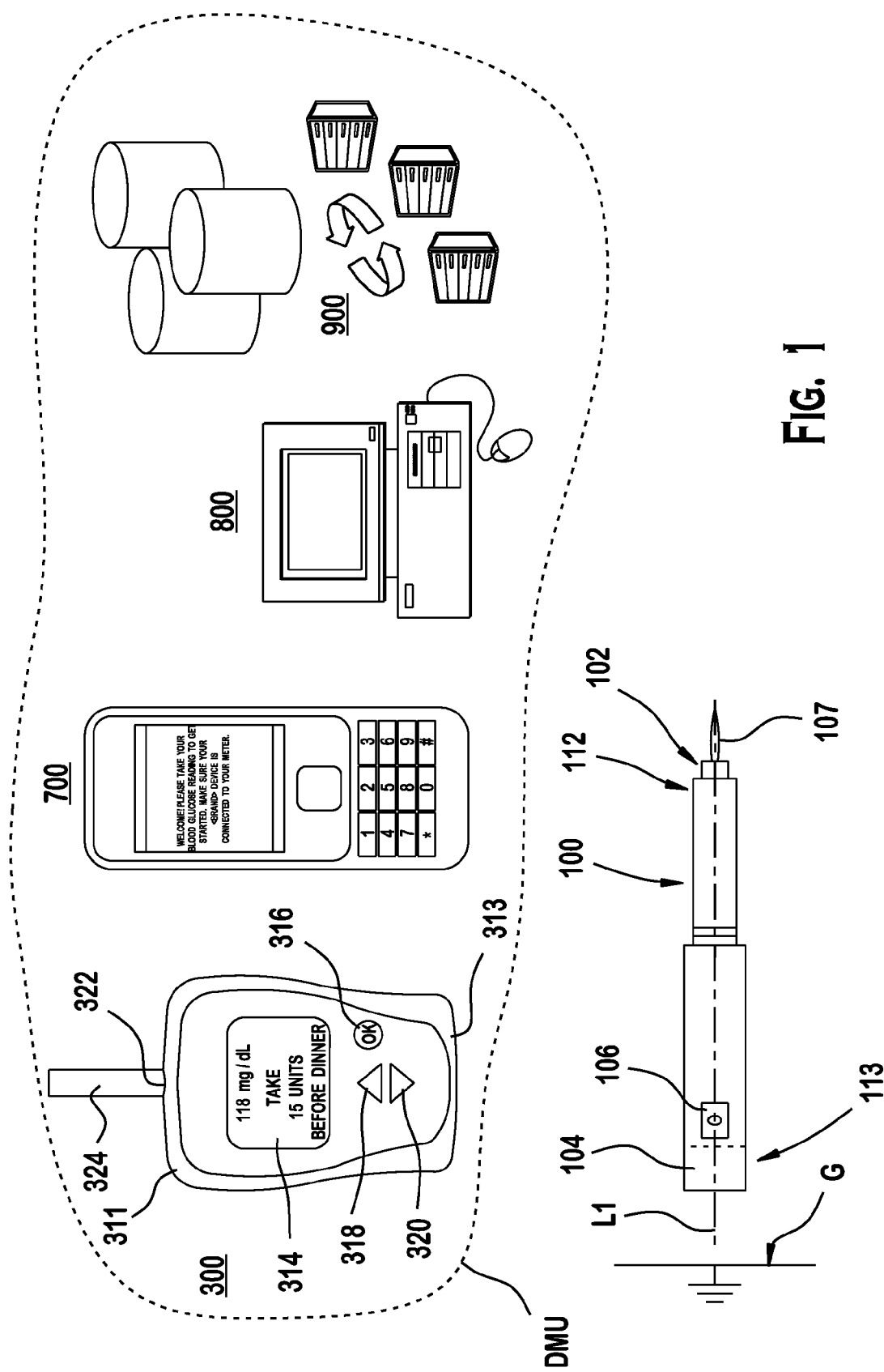
FIG. 1 illustrates a system that includes a first type of drug delivery pen and a plurality of data management units, according to an exemplary embodiment described and illustrated herein.

FIG. 1 illustrates a diabetes management system that includes a drug delivery pen 100 configured to wirelessly communicate with a data management unit or DMU such as, for example, a glucose meter 300, a mobile phone 700, a personal computer 800 (including a mobile computer), or a network server 900, or through a combination of the exemplary data management unit devices described herein. As used herein, the nomenclature "DMU" represents either individual unit 300, 700, 800, or 900 separately or all of the data management units (300, 700, 800, 900) usable together in a disease management system.

Drug delivery pen 100 may have a generally tubular pen housing that extends from a first end 112 and a second end 113 along a longitudinal axis L1, as shown in FIG. 1. The first end 112 of the housing may enclose or is connected to a cartridge 150 that is configured to contain a drug 153 such as, for example, insulin or other drugs (FIG. 3).

Figure 3:
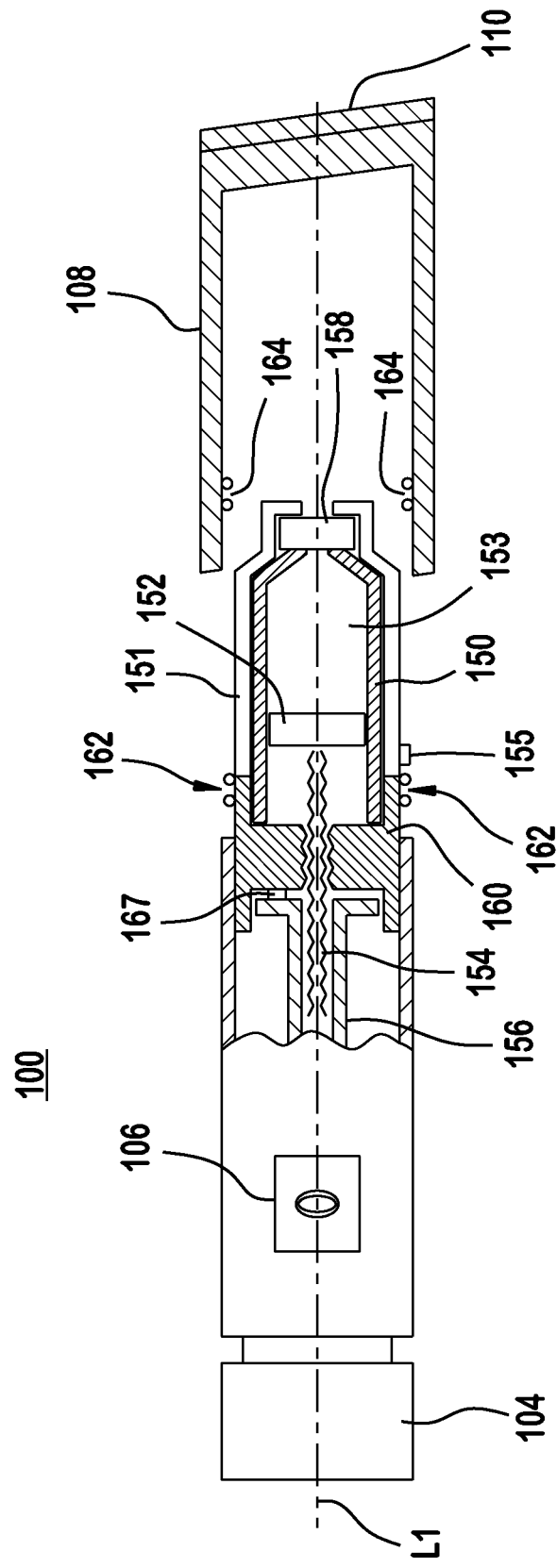
FIG. 3 illustrates a simplified partial cross-sectional view of the drug delivery pen in FIG. 1, according to an exemplary embodiment described and illustrated herein.

As seen in FIG. 3, one end of cartridge 150 can be sealed by a piston 152 where movement of piston 152 causes the drug 153 to be dispensed. Needle portion 102 can be configured to hold a needle 107 so that a user can inject insulin with drug delivery pen 100. The second end 113 of the pen housing may have a knob 104 that is operatively coupled to piston 152 (FIG. 3). The dosage display 106 may output the amount of fluid dispensed on a display screen such as a printed display or a liquid crystal display (LCD), as illustrated in FIGS. 1 and 3.

Pen 100 may include a mechanism to dispense a controlled volume of fluid from cartridge 150. Rotation of knob 104 in a clockwise or counterclockwise direction can cause knob 104 to telescope inward and outward with respect to the pen housing. Such rotation can control a user-selected amount of drug 153 or bio-effective fluid to be dispensed via motion of a piston rod 154. A depression of knob 104 along axis L1 can initiate the dispensing of the selected amount of fluid or drug 153 via piston rod 154 and piston 152.

Pen 100 may include a dosage sensor to monitor both the inward and outward movement of knob 104 for monitoring the activity of the drug delivery pen. The dosage sensor can be any suitable sensor that can measure linear or rotational motion of the piston rod 154 along axis L1. The sensor is preferably a linear potentiometer and is used to measure the position of knob 104 along axis L1 for determining the size of the bolus injected by the user. The sensor is electrically coupled to an analog-to-digital converter, which is coupled to a microprocessor board to provide data on the position of knob 104 or piston rod. Other sensors that may be used with the exemplary embodiments include rotational potentiometers, linear or rotational encoders, capacitive sensor, optical displacement sensor, magnetic displacement sensor, or combinations and equivalents thereof.

Referring again to FIG. 3, drug delivery pen 100 includes a ratchet 156, a piston rod 154, a nut 160, a piston 152, and a cartridge holder 151. Cartridge holder 151 can be configured to hold a cartridge 150, where the cartridge contains one or more drugs such as, for example, insulin and a biologically effective agent. Cartridge 150 can include a septum 158 that can be configured to hold a needle (needle not shown in FIG. 3). Piston rod 154 can be configured to have a non-circular cross-section and a threaded outer surface, which is guided by ratchet 156. When activating a dosage, ratchet 156 and piston rod 154 are influenced to cause piston rod 154 to move piston 152. Movement of piston 152 causes the drug 153 to be dispensed from pen 100. Piston rod 154 can be configured to be displaceable along axis L1 of pen 100, but not rotatable along the longitudinal axis. Nut 160 can include sensors for monitoring the size of the injected dose. Nut 160 can be rotatable along the longitudinal axis, but not displaceable along the axis. Nut 160 can have an inner thread that is keyed to correspond to the outer thread of piston rod 154. Nut 160 and piston rod 154 can be configured so that the axial movement of piston rod 154 is unidirectional for dispensing insulin. In general, rotational movement of piston rod 154 during drug ejection can be achieved as described in U.S. Pat. No. 6,235,004, which is hereby incorporated by reference herein and attached hereto in the Appendix.

Referring to FIG. 3, the cartridge holder 151 may have a suitable identifier 155 embedded or fixed to the cartridge holder 151 or even with the cartridge 150. In one embodiment, the identifier 155 can be a Radio-Frequency-Identification (RFID) tag that is programmed to store information such as, for example, information regarding the drug or bio-active fluid 153 in the cartridge 150, date of manufacture, manufacture's name, date of expiration, batch identifier, calibration data, custom identifier and the like. Where the identifier 155 is in the form of the RFID, a RFID reader 157 can be used to read the information stored in the RFID 155. The RFID reader 157 can be coupled to the processor 170 of circuit board 178 on the pen itself. In another embodiment, the RFID reader 157 can be coupled to the processor of the DMU. Alternatively, the RFID reader 157 can be utilized in both the pen and the DMU.

Figure 2:
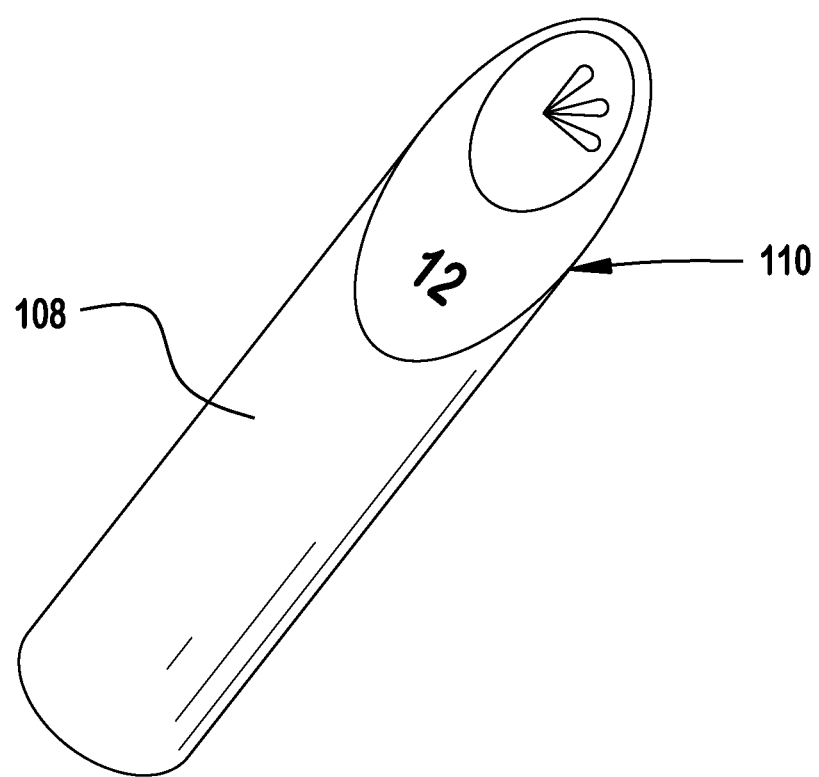
FIG. 2 illustrates a perspective view of a cap configured to mate with the drug delivery pen in FIG. 1, according to an exemplary embodiment described and illustrated herein.

Drug delivery pen 100 can be configured to couple to a cap 108, as illustrated in FIGS. 2 and 3. Cap 108 can include a display 110 and corresponding switches 164. Cap 108 can cover needle portion 102 to prevent contamination of the needle and septum, and to avoid accidental needle sticks. FIG. 3 illustrates a partial cross-sectional view of drug delivery pen 100 mated with cap 108. When cap 108 is mated to or removed from pen 100, corresponding switches 164 can interact with electrical switches 162 on pen 100 so that a microprocessor can recognize a beginning and end of pen activity.

Figure 5:
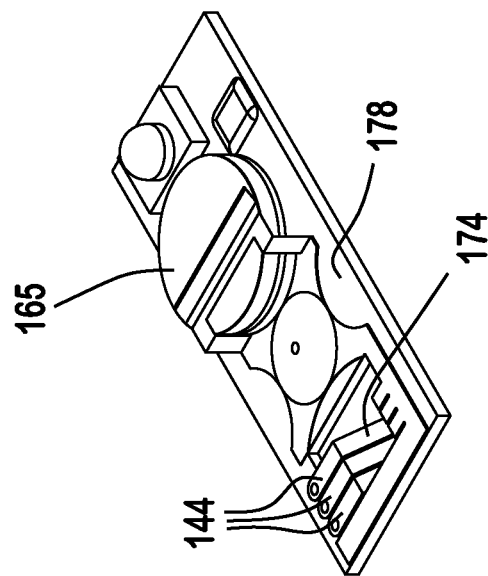
FIG. 5 illustrates a perspective view of a circuit board of the drug delivery pen of FIG. 1, according to an exemplary embodiment described and illustrated herein.
Figure 4:
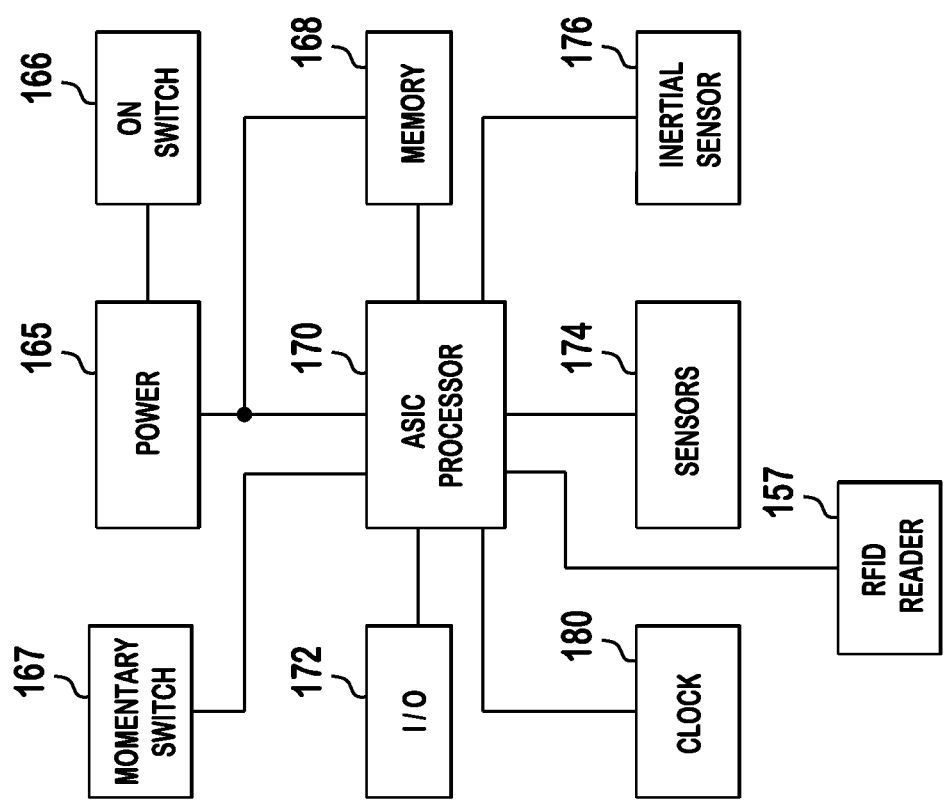
FIG. 4 illustrates a schematic of the electrical components of the drug delivery pen of FIG. 1, according to an exemplary embodiment described and illustrated herein. Note: Label in FIG. 4 should say "Momentary Switch" (not Moment switch)

FIG. 4 illustrates electronic components that can be included on circuit board 178 such as a battery 165, a sensor 174, an on switch 166, momentary micro switch 167, a memory 168, an application specific integrated circuit (ASIC) 170, input/output port 172, a clock 180, and an accelerometer or inertial sensor 176. Alternatively, circuit board 178 can be replaced with a flex circuit. On switch 166 can be used to allow battery 165 to deliver power to ASIC 170. ASIC170 can be connected to battery 165, memory 168, input/output port 172, sensors 174, and accelerometer or inertial sensor 176. Sensors 174 can be configured to detect a quantity of an ejected dose, which is communicated to ASIC 170. A portion of sensors 174 can be in the form of three fingers 144 which can measure the rotational movement of knob 104. The ejected dose information can be saved to memory 168 by ASIC 170. Input/output port 172 can be configured to communicate data to an external device such as a cell phone, a personal computer, or a glucose meter. Alternatively input/output port 172 can be in the form of a wireless transceiver to wirelessly communicate data to an external device such as a cell phone, a personal computer, or a glucose meter. Accelerometer or inertial sensor 176 can be included on circuit board 178 for measuring movement and orientation of pen 100. Accelerometer or inertial sensor 176 can be configured for determining if pen 100 was primed properly, whether insulin types were mixed properly in pen 100, or if pen 100 should come out of sleep mode. FIG. 5 illustrates an exemplary circuit board 178 with components described in FIG. 4, in which the board 178 may be disposed in a housing of pen 100.

Other electrical circuit components (not shown due to placement of components in the drawings) that may be disposed on board 178 can include, an analog-to-digital converter, a speaker, a display, a display driver, a user interface driver, a wireless module in the form of a transmitter, a receiver or a transmitter-receiver (e.g., a wireless transceiver using infrared light, radio-frequency, or optical waves) to communicate with a wireless module of the data management unit DMU, and an antenna to send and receive wireless signals, process input from the sensor, turn the device on and off, put the device into sleep mode, wake the device up, regulate power from the battery, and store and retrieve information to and from memory, as examples.

Figure 13:
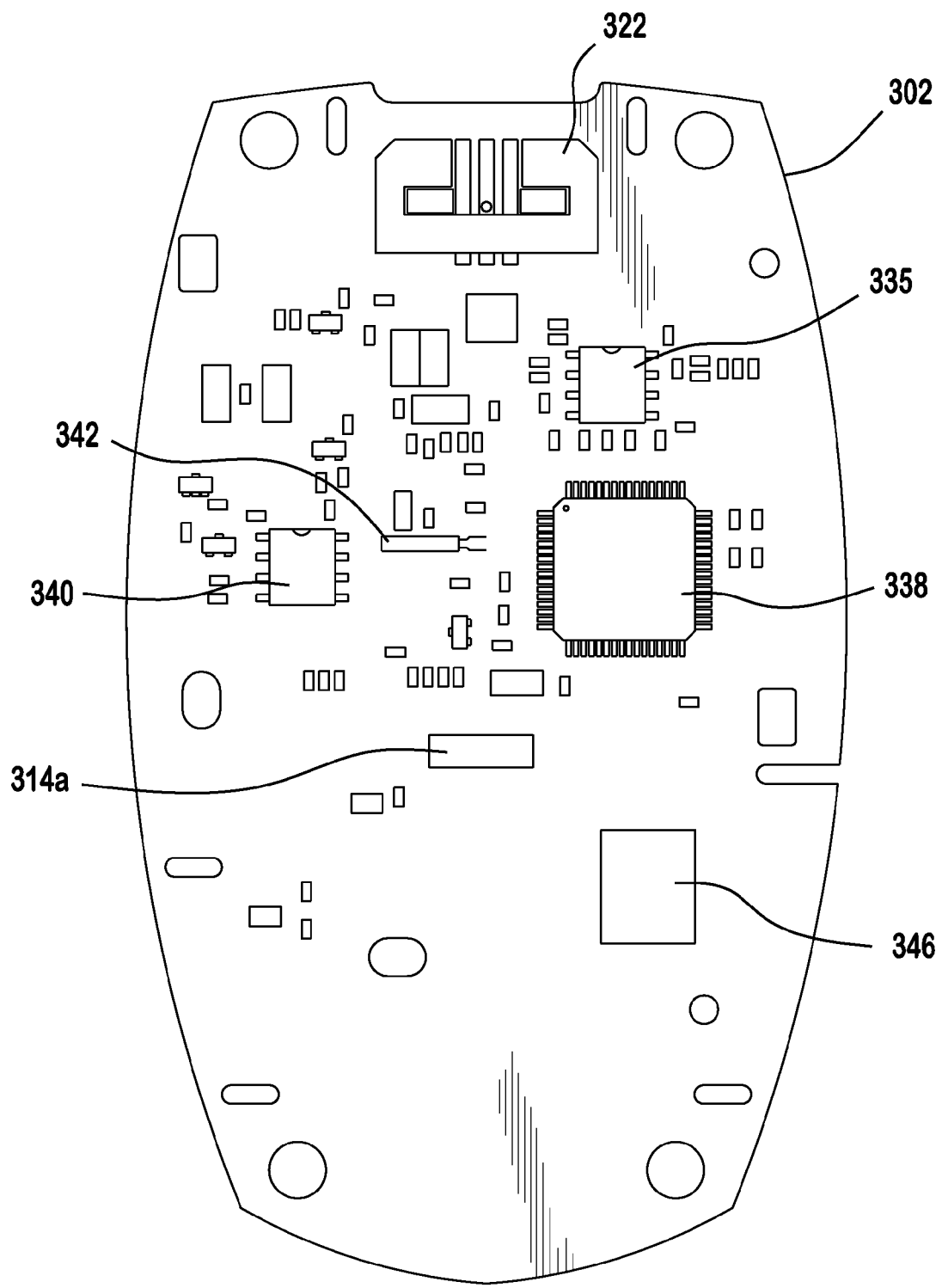
FIG. 13 illustrates a top portion of a circuit board of the glucose meter of FIG. 1, according to an exemplary embodiment described and illustrated herein.
Figure 14:
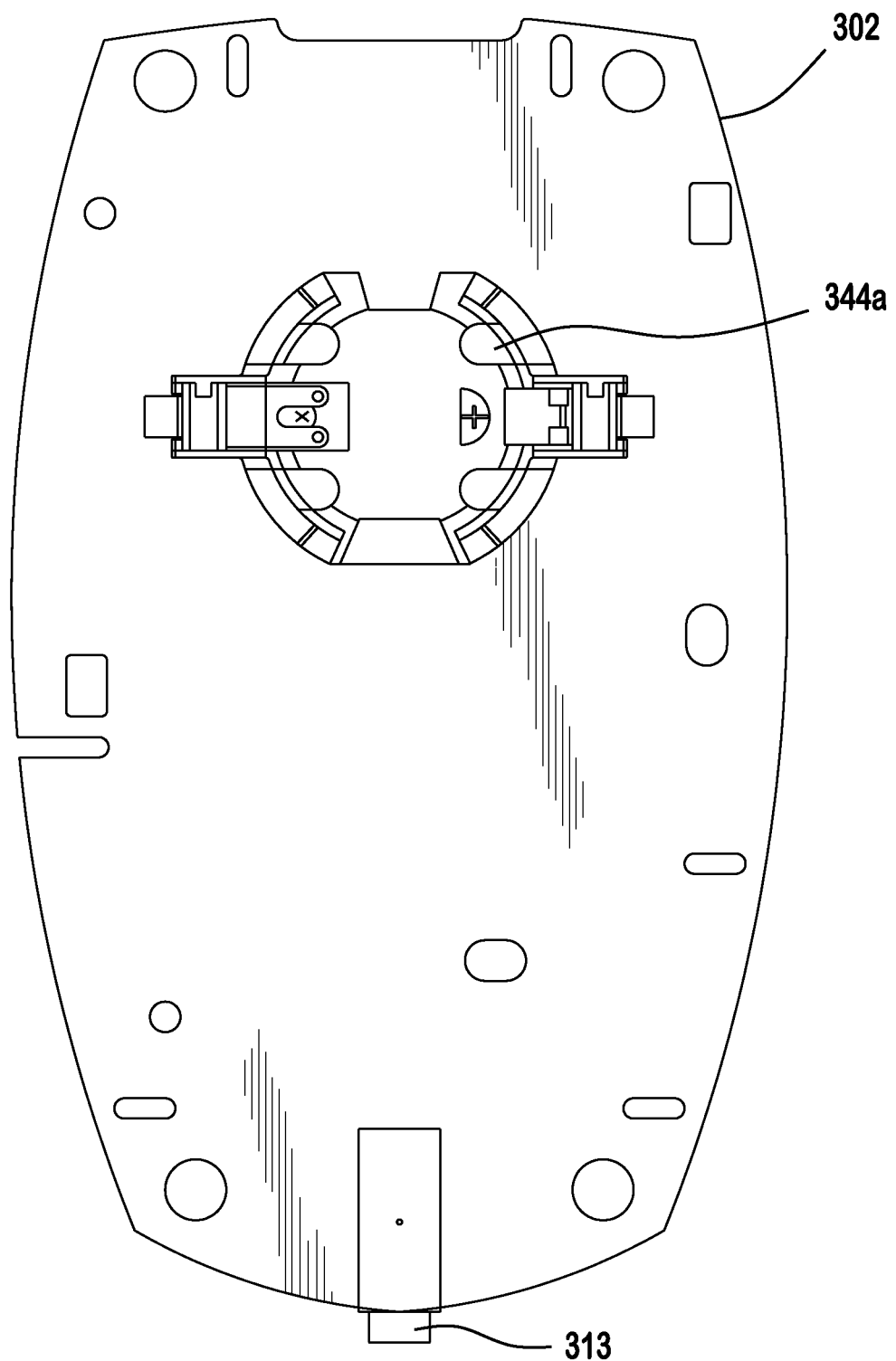
FIG. 14 illustrates a bottom portion of a circuit board of the glucose meter of FIG. 1, according to an exemplary embodiment described and illustrated herein.

In one embodiment, the data management unit DMU is in the form of a glucose meter 300, which can include a housing 311, user interface buttons (316, 318, and 320), a display 314, a strip port connector 322, and a data port 313, as illustrated in FIGS. 1, 13, and 14. User interface buttons (316, 318, and 320) can be configured to allow the entry of data, navigation of menus, and execution of commands. Data can include values representative of analyte concentration, and/or information, which are related to the everyday lifestyle of an individual. Information, which is related to the everyday lifestyle, can include food intake, medication use, occurrence of health check-ups, and general health condition and exercise levels of an individual. Specifically, user interface buttons (316, 318, and 320) include a first user interface button 316, a second user interface button 318, and a third user interface button 320.

The electronic components of meter 300 can be disposed on a circuit board 302 that is within housing 311. FIGS. 13 and 14 illustrate the electronic components disposed on a top surface and a bottom surface of circuit board 302. On the top surface, the electronic components include a strip port connector 322, an operational amplifier circuit 335, a microcontroller 338, a display connector 314a, a non-volatile memory 340, a clock 342, and a first wireless module 346. On the bottom surface, the electronic components include a battery connector 344a and a data port 313. Microcontroller 338 can be electrically connected to strip port connector 322, operational amplifier circuit 335, first wireless module 346, display 314, non-volatile memory 340, clock 342, power supply 344, data port 313, and user interface buttons (316, 318, and 320).

Operational amplifier circuit 335 can be two or more operational amplifiers configured to provide a portion of the potentiostat function and the current measurement function. The potentiostat function can refer to the application of a test voltage between at least two electrodes of a test strip. The current function can refer to the measurement of a test current resulting from the applied test voltage. The current measurement may be performed with a current-to-voltage converter. Microcontroller 338 can be in the form of a mixed signal microprocessor (MSP) such as, for example, the Texas Instrument MSP430. The MSP430 can be configured to also perform a portion of the potentiostat function and the current measurement function. In addition, the MSP430 can also include volatile and non-volatile memory. In another embodiment, many of the electronic components can be integrated with the microcontroller in the form of an application specific integrated circuit (ASIC).

Strip port connector 322 can be configured to form an electrical connection to the test strip. Display connector 314a can be configured to attach to display 314. Display 314 can be in the form of a liquid crystal display for reporting measured glucose levels, and for facilitating entry of lifestyle related information. Data port 313 can accept a suitable connector attached to a connecting lead, thereby allowing glucose meter 300 to be linked to an external device such as a personal computer. Data port 313 can be any port that allows for transmission of data such as, for example, a serial, USB, or a parallel port. Clock 342 can be configured for measuring time and be in the form of an oscillating crystal. Battery connector 344a can be configured to be electrically connected to a power supply in the form of a battery (not shown).

In one embodiment, test strip 324 can be in the form of an electrochemical glucose test strip. Test strip 324 can include one or more working electrodes and a counter electrode. Test strip 324 can also include a plurality of electrical contact pads, where each electrode is in electrical communication with at least one electrical contact pad. Strip port connector 322 can be configured to electrically interface to the electrical contact pads and form electrical communication with the electrodes. Test strip 324 can include a reagent layer that is disposed over at least one electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration. The working electrode can then measure a concentration of the reduced mediator in the form of a current. In turn, glucose meter 300 can convert the current magnitude into a glucose concentration.

By virtue of the configurations described exemplarily herein, applicants have now been able to provide the means for determining the difference between either or both of a dosage delivery event and duration of such dosage delivery or injection event. Specifically, where a user is merely rotating knob 104 to thereby move knob 104 along a longitudinal axis, the pen does not measure the occurrence of a dosage event. Except for a determination that a dosage selection is being made, no recording is made in the memory of the processor board regarding a dosage delivery. Only upon the full depression of knob 104 would a momentary switch coupled to the knob 104 in the pen be activated, triggering a determination that dosage delivery is taking place. In an embodiment, the electronics can be configured to go into "sleep" mode, until knob 104 is depressed, which reduces the power consumption of the module. In another embodiment, the electronics can be configured to go into "sleep" mode, until the inertial sensor determines that the pen has been moved. As used herein, the "sleep" mode is one in which all functionalities of the module are at minimal or virtually zero power consumption but which does not require a system boot up in the event that the pen is taken out of sleep mode.

It should be noted that the use of a momentary microswitch (e.g., switch 167) also enables tracking of the injection start point and the injection end point, so the volume of the injection can be calculated, even if the user does not press the knob all the way to the zero or initial dosage position. While the ability to determine when a dosage delivery has been made is valuable to a user in managing diabetes, applicants believe that it is the ability to determine and confirm the duration of such dosage delivery that is a step forward in the art of diabetes management. In other words, a combination of depression of the momentary switch, detection of the plunger moving, detection of an actual injection, and determination by the dosage sensor of how much is delivered that provides for an identification of the actual dosage delivered to the user (Note that the rate of injection will vary depending on how hard the user presses the button) which can be used for later analysis with a compliance regiment. Thus, where a patient is injecting insulin per a protocol as prescribed by a health care provider, such patient may not be in full compliance if the patient fails to deliver a complete prescribed dosage, which typically requires fully depressing knob 104 for four (4) to ten (10) seconds. By recording the dosage, time and duration in a memory of processor board for display on the module itself, the data management unit DMU, or even for transfer and display on a health care provider's computer, the health care provider is able to take steps, after review of data or even in real-time, to ensure that full compliance of the prescribed protocol is followed. In the preferred embodiments, a warning or reminder to the patient on proper pen usage technique can be displayed as a message on the data management unit, which in one embodiment includes a glucose meter. In an alternative, the health care provider or an automated monitoring service would issue a warning to the user via email, text messaging or even a call to the user's mobile phone or computer.

Second Type of Drug Delivery Pen

Figure 6:
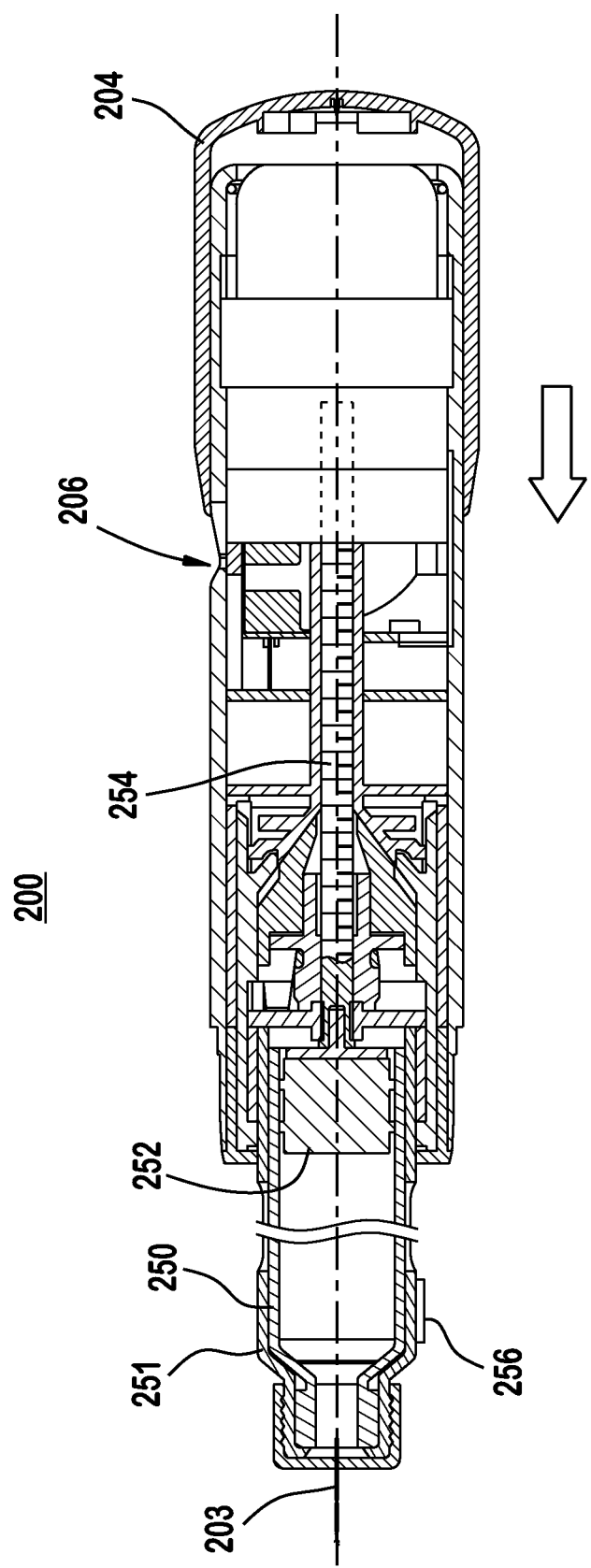
FIG. 6 illustrates a cross-sectional view of a second type of drug delivery pen, according to an exemplary embodiment described and illustrated herein.

FIG. 6 illustrates a cross-sectional view of a second type of drug delivery pen 200 that includes a needle 203, a cartridge holder 251, a cartridge 250, a piston 252, and a piston rod 254, a knob 204, and a display window 206. Knob 204 can be rotated to dial in a predetermined insulin dosage. Display window 106 can show the predetermined quantity (i.e., dosage amount). Rotation of knob 204 mechanically influences the amount of travel that piston 252 and piston rod 254 can move when dosing insulin. Knob 204 can also be pushed in an axial direction for causing insulin to be dispensed from cartridge 250. Similar to the previous embodiment, the cartridge 250 is provided with an RFID 256 that is programmed with data. The data stored in the RFID 256 can be read by an RFID reader 257 disposed on circuit board 278 for operative connection to the processor of the pen. A description of pen 200 can also be found in U.S. Pre-Grant Publication No. 2007/0021715, which is hereby fully incorporated by reference with a copy provided in the Appendix.

Similar to pen 100, pen 200 also includes an electronic assembly for monitoring the use of the pen, as illustrated in FIG. 7. FIG. 8 illustrates an exploded perspective view of the electronic assembly that includes a receptacle 286, battery contacts 284, a battery 264, a circuit board 278, a LED 282, microprocessor 290, accelerometer or inertial sensor 276, and a momentary switch 267 connected to the processor 290. Momentary micro-switch 267 can be activated when knob 204 is depressed in an axial direction (FIG. 7). Receptacle 286 can be used as a framework for holding battery 264 and circuit board 278. Circuit board 278 can be sandwiched in between battery 264 and momentary microswitch 267. Several electronic components can be mounted to circuit board 278 such as LED 282, momentary micro-switch 267, and microprocessor 290, as shown in FIG. 8. Note that circuit board 278 is orientated in a stacking relationship with the switch and the battery allowing the pen housing to be generally symmetrical along the longitudinal axis. Other components that can be mounted to circuit board 278 are a wireless transceiver, a clock, a memory, sensors, and an accelerometer 276.

Third Type of Drug Delivery Pen

Figure 9:
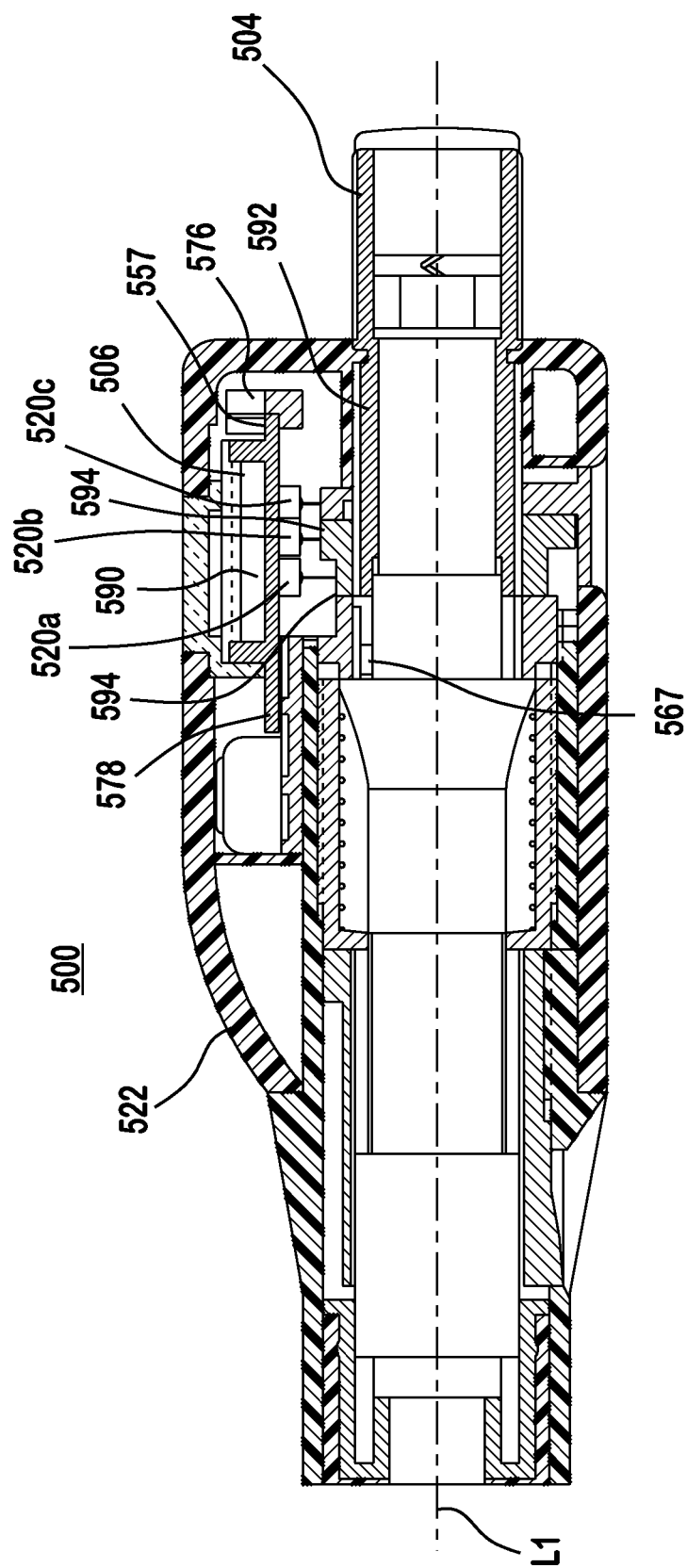
FIG. 9 illustrates a cross-sectional view of a third type of drug delivery pen, according to an exemplary embodiment described and illustrated herein.

FIG. 9 illustrates a cross-sectional view of a third type of drug delivery pen 500 that has an asymmetric housing. Pen 500 has a generally cylindrical housing with a casing 522 that contains a sensor and electronic components for measuring the activity of the pen. Pen 500 includes a knob 504 that is rotatable along a longitudinal axis L1 of the pen. Rotation of knob 504 can be configured for setting a dosage amount of insulin that is shown in a display window 506. Pressing down of knob 504 into the pen housing causes a sleeve 592 to move relative to the housing, which in turn, causes insulin to be dispensed and a momentary microswitch 567 to be actuated. Casing 522 can be configured to contain a circuit board 578. Casing 522 can include three wall surfaces that together with the outer surface of the pen housing provide for enclosure of certain components. Several electronic components can be mounted to circuit board 578 such as a sensor 520 and microprocessor 590, as shown in FIG. 9. Other components that can be mounted to circuit board 578 include a wireless transceiver, a clock, a memory, and an accelerometer 576. Sensor 520 can include a plurality of laser detectors such as laser detectors 520a, 520b, and 520c. The laser detectors can measure reflected light of a profile area 594 that corresponds to a predetermined dosage amount that is dialed in with knob 504. Similar to the prior embodiments, a drug cartridge (not shown for brevity) is connected to the pen housing and provided with an RFID tag for data collection by the pen or by a DMU. A description of pen 500 can also be found in U.S. Pre-Grant Publication No. 2006/0224123, which is hereby fully incorporated by reference and a copy is attached herewith in the Appendix.

Fourth Type of Drug Delivery Pen

Figure 10:
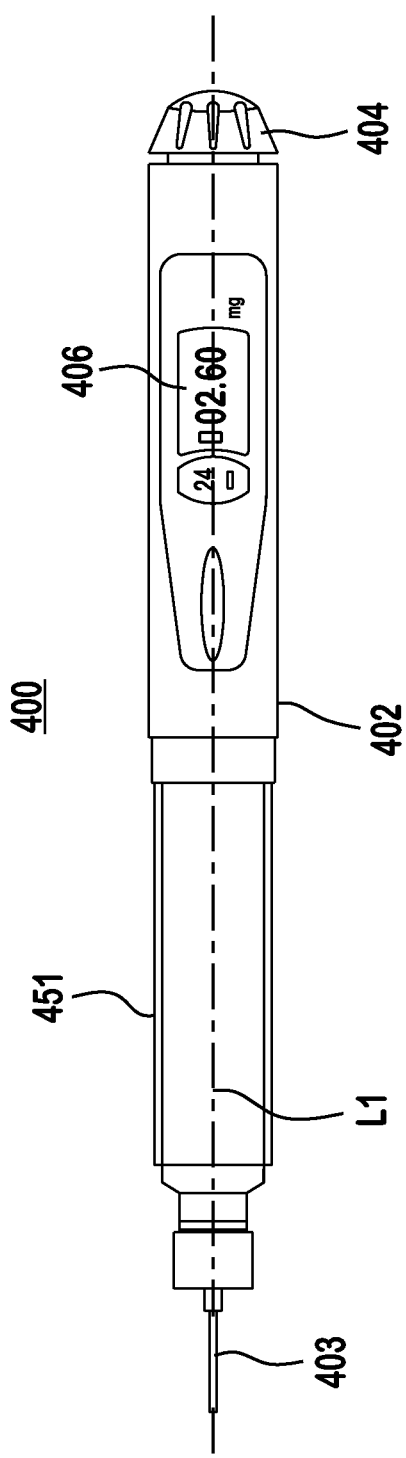
FIG. 10 illustrates a side view of a fourth type of drug delivery pen, according to an exemplary embodiment described and illustrated herein.
Figure 11:
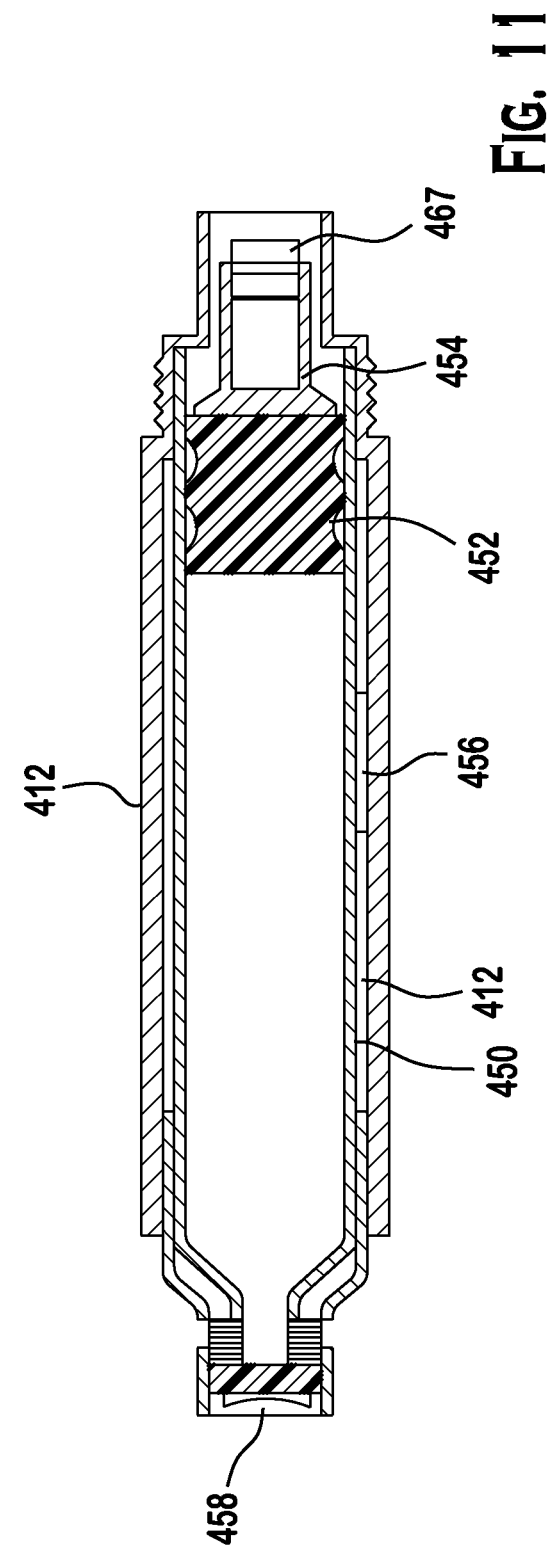
FIG. 11 illustrates a cross-sectional view of a cartridge holder of the drug delivery pen of FIG. 10, according to an exemplary embodiment described and illustrated herein.
Figure 12:
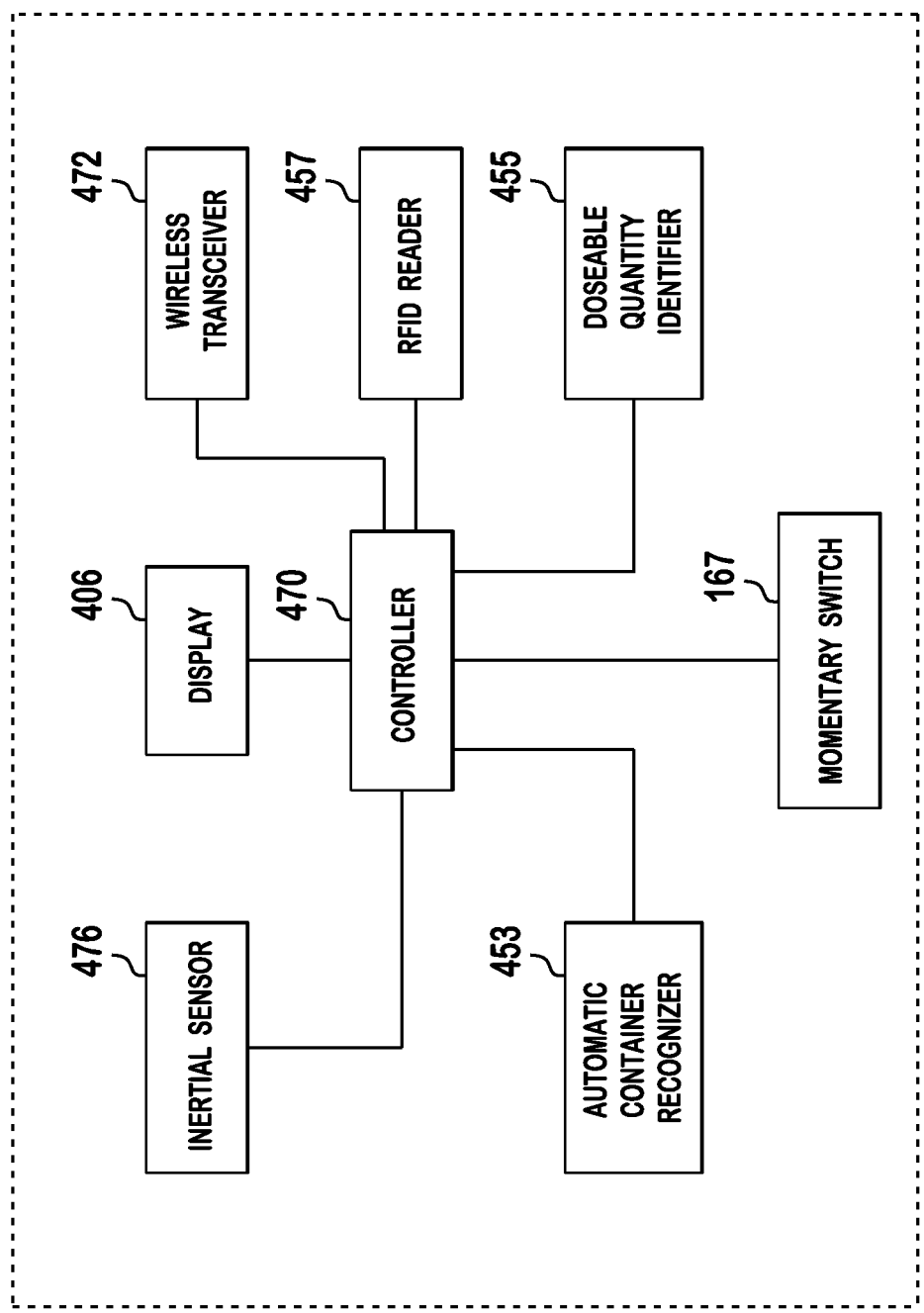
FIG. 12 illustrates a schematic of the electrical components of the drug delivery pen of FIG. 10, according to an exemplary embodiment described and illustrated herein.

FIG. 10 illustrates a side view of a fourth type of drug delivery pen 400 that includes a housing 402 extending along longitudinal axis L1. The housing 402 may have needle 403, a cartridge holder 451, a display window 406, and a knob 404. FIG. 11 illustrates a side cross-sectional view of the cartridge holder 451 that includes a septum 458, a barrel 412, a cartridge 450, a piston 452, and a piston rod 454. Rotating knob 404 along longitudinal axis L1 allows a user to set a dosage amount. Pressing down on knob 404 along the longitudinal axis causes momentary switch 467 to be actuated and at the same time causing piston 452 to move, which in turn, causes insulin to be dispensed from needle 403. FIG. 12 shows a simplified schematic of electronic components that can be contained within a housing of pen 400. The electronic components include an accelerometer 476, a display 406, a wireless transceiver 472, a microcontroller 470, an automatic container recognizer 453, and a doseable quantity identifier 455. Automatic container recognizer 453 can function to recognize a characteristic of a container inserted into pen 400 and then input that information to microcontroller 470. Automatic container recognizer 453 can be in the form of an optical, electrical, or mechanical sensor for recognizing corresponding indicia on cartridge 450. Doseable quantity identifier 455 can function to recognize a dosage amount set by a user through rotating knob 404 and then input that information to microcontroller 470.

Operation of the Exemplary Embodiments

The system described herein can be used to provide clinical benefits for persons with diabetes. In one example, a health care provider ("HCP") can set up a therapeutic protocol in the DMU 300 by logging in to an HCP selection menu by entry of a password, or for greater security, via the use of a cryptographic security key such as, for example, a USB security PKI token. Alternatively, the logging in process can be conducted via a secure remote terminal or mobile phone 700, computer 800, or network server center 900 and performing the menu selection remotely. Upon successful log in, the HCP can select one of a plurality of therapeutic protocols, such as, for example "Long-Acting" protocol; "Mix" protocol or Multiple Daily Injection ("MDI") protocol.

Where the protocol selected is the Long-Acting protocol, the HCP would select the weight range of the user and confirm that the starting and maximum doses are correct with the preferred blood glucose test being performed after fasting and the insulin being delivered to the user's body at bedtime. Thereafter, the protocol is then transferred, by cables or via short or long-range wireless connection to the user's DMU 300.

Where the protocol selected is the Mix protocol, the HCP would select the frequency of insulin delivery over a fixed time period. Here, the HCP would need to confirm the insulin regimen as being of the selected frequency over a fixed duration but at specified time in a day. Thereafter, the protocol is then transferred, by cables or via short or long-range wireless connection to the user's DMU 300.

Where the protocol selected is the MDI protocol, the HCP would select the largest meal that the user would have during the day and confirm the regimen with the required dosages for rapid acting at specified daily event and rapid acting at a different daily event. Thereafter, the protocol is then transferred, by cables or via short or long-range wireless connection to the user's DMU 300.

At DMU 300, the user whose HCP has selected a Long-Acting protocol would see a series of interactive screens. The processor of the DMU 300 would generate a greeting message and a reminder consistent with the protocol, which has been transferred from the HCP's computer 800 or network server center 900 to the memory. At this point the user should perform a blood glucose test using a test strip 324 with an analyte test meter, which in this case is DMU 300. Upon analysis, the analyte test device would provide an output of the measured glucose concentration on the display screen 314. Thereafter, the processor would generate a message on display 314 indicating the dosage needed for the physiological requirements of the user. At this stage, the user is given the option of selecting a reminder of when to take the required dosage of therapeutic agent. Here, it is preferred that the default selection is that of a reminder being activated. At the option of the user, various screens can be generated to provide a summary of blood glucose test, trends, therapeutic type and dosage taken. In one example, a summary of the therapeutic agent and the type of therapeutic agent taken at a particular time and date can be displayed.

At DMU 300, the user whose HCP has selected a Mix protocol would see a series of interactive display messages. In one message, the processor 1706 would generate a greeting message and a reminder consistent with the protocol, which has been transferred from HCP's computer 800 or network server center 900 to the memory of glucose meter 300. At this point the user should perform a blood glucose test using test strip 324 with a suitable analyte test meter, which in this case, can be DMU 300. Upon analysis, the device would provide an output of the measured glucose concentration on display 314. Thereafter, the processor would generate a message at the display 314 indicating the dosage needed for the physiological requirements of the user. Here, the user is given the option of selecting a reminder of when to take the required dosage of therapeutic agent. At this point, it is preferred that the default selection is that of a reminder being activated. At the option of the user, various display screens can be generated to provide a summary of blood glucose test, trends, therapeutic type and dosage taken. In one example, a summary of the therapeutic agent and the type of therapeutic agent taken at a particular time and date can be provided.

At DMU 300, the user whose HCP has selected a MDI protocol would see a series of interactive display screens. At one screen, the processor of glucose meter 300 would generate a greeting message and a reminder consistent with the protocol, which has been transferred from HCP's computer 800 or network server center 900 to the memory of glucose meter 300. At this point the user should perform a blood glucose test using test strip 324 with a suitable analyte test meter, which in this case, can be DMU 300. Upon analysis, the device would provide an output of the measured glucose concentration on display screen 314. Thereafter, the processor would generate a message indicating the dosage needed for the physiological requirements of the user. Here, the user is given the option of selecting a reminder of when to take the required dosage of therapeutic agent. At this point, it is preferred that the default selection is that of a reminder being activated. At the option of the user, various screens can be generated to provide a summary of blood glucose test, trends, therapeutic type and dosage taken. In one example, a summary of the therapeutic agent and the type of therapeutic agent taken at a particular time and date can be provided.

To ensure that the user follows the therapeutic regimen, the DMU 300 in conjunction with the drug delivery pen can be used to ensure compliance of the regimen by reminding the user of the therapeutic agent dosage needed based on the measured pre-meal blood glucose value or prompting the user at the specified time to deliver the required dosage for the user. As part of the prompting or reminding, the RFID reader in the pen or the DMU can poll the RFID tag embedded with the drug cartridge to determine relevant information such as, for example, type of drug(s) in the cartridge, volume of drug in the cartridge, expiration date, batch date, manufacturer identification and the like. The information collected from the RFID tag are then compared with the protocol to ensure that the drug or biologic prescribed by the HCP is the correct one being used by the patient. Thereafter, a log is recorded of the data collection from the RFID tag to the RFID reader in the memory of the pen or DMU. In the event of information mismatch such as, for example, the drug identified by RFID tag of the cartridge is not the correct drug being prescribed by the HCP as loaded into the DMU, an alert (e.g., alarm, signal, or even an alert to the HCP via a mobile phone signal) can be provided to ensure the safety of the patient or user. Once the DMU has made the determination that the drug cartridge is the proper drug prescribed by the HCP in the protocol stored in the DMU via the RFID tag and reader, the DMU 300 can be configured to detect activation of the drug delivery pen by the removal of the cap, movement of the pen using an accelerometer, and rotation of the knob, or pushing of the knob. Upon detection of activation or actual delivery of the therapeutic agent by the drug delivery pen via transmission of a wireless signal to the DMU 300, a message can be provided on DMU 300 (or mobile phone 700, computer 800, and network server center 900) to indicate the dosage and time of the administration of the therapeutic agent. It should be noted that while an RFID tag in the form of a microchip with an antenna and RFID reader are utilized in the preferred embodiments, any suitable micro device that can store data and be sufficiently small to be attached to a drug cartridge can be utilized in place of the RFID tag. Likewise, any wireless polling device that can be used to remotely access the information in the storage medium can be utilized in place of the RFID reader.

Another approach to ensure the correctly prescribed or recommended drug or cartridge can be performed as follows: programming the DMU to set a reminder on the DMU screen upon activation of the DMU or pen to check for insulin type in the drug cartridge, if there is a mismatch, entering the correct insulin type (rapid acting insulin, long acting insulin, or premixed insulin) and setting a safety check feature on the DMU for rapid acting insulin, e.g., such as by setting a maximum dose 30 U or less. In the event that the user accidentally injects the insulin more than the maximum dose, the DMU will remind the user to take some actions to minimize the effect of the overdose, e.g. to suggest measure blood glucose and take some food to counteract the effect of insulin.

To utilize the drug delivery pen in the method described above, a user would rotate the knob, which allows the user to dial in a dosage for injection. The selected dosage appears in the dosage indicator window of the pen. As the knob rotates, it telescopes outward or inward with respect to the pen housing. The amount of insulin to be injected is proportional to the outward extension of the knob, which is measured by the dosage sensor. This information can then be retained in the memory of the pen or transmitted to the DMU to ensure that the correct dosage has been followed. In the event that the dosage amount selected is unsafe based on historical record of the user, a warning beep can be provided in the pen or in the DMU. Where the dosage selected may be dangerous, or the wrong type of drug is being injected, an alarm can be sent to the DMU which can transfer this alarm to a HCP or a caretaker (e.g., parents, teacher, nurses, guardian, or the like) for immediate follow up with the user.

A suitable needle (e.g., 203) can be attached to the insulin cartridge 250. Before injecting, the user primes the drug delivery pen by ejecting a small dose (typically 2 Units) before inserting a needle subcutaneously. Priming drug delivery pen eliminates bubbles. The purpose of priming (sometimes called a test injection) is to remove air bubbles from the drug cartridge and the needle, which would reduce the volume of an injection. Failure to remove air bubbles can cause the pen to dose inaccurate volumes, which can be especially significant when small doses are being delivered, for example, to children. The drug delivery pen should be held generally vertically such that the drug cartridge and the needle are generally topmost with respect to the ground G (FIG. 1) during priming so bubbles rise to the top of the drug cartridge (the end closest to the needle) and may be expelled by a priming dose. The priming is successful if the user sees a drop of insulin appear at the needle tip. If the user does not see a drop of insulin, the priming step is repeated. An inertial sensor is disposed in the pen housing or located on the processor board to detect if the drug delivery pen is held vertically during priming, and this information may be sent wirelessly to the data management unit. Low cost microelectromechanical systems (MEMS) inertial sensor chips are widely available, accurate, low cost, and small in size. Preferred inertial sensor may include Analog Devices model ADXL322 accelerometer (available at http://www.analog-.com/en/mems-and-sensors/imems-accelerometers/ADXL322/products/produc.html#pricing). The drug delivery pen may distinguish between primes and injections by one of two exemplary techniques or a combination of the two techniques: (1) it may determine via an inertial or acceleration sensor disposed in the pen housing whether the drug delivery pen is held with needle pointing upward by the rotation and acceleration of the pen about the axis orthogonal to the longitudinal axis L1 to determine if the pen is undergoing priming and (2) it can use software to determine if one or more small doses of approximately 2 Units are followed by a larger dose. For example, a gravity or inertial sensor may be used to determine if the device is pointing upwards when the knob is pressed, indicating a priming shot since the device is held in an inverted position when purging bubbles. The pen is able to distinguish priming shots from actual drug delivery. For example, priming shots are typically two units or less, making them distinguishable from larger injected shots, and a priming shot will typically be followed by an injected shot, a pattern that may be distinguished in software. Similarly, it is useful to be able to distinguish between dosage size adjustments in which the user turns the dial backwards and/or forwards to dial in a specific dosage versus movement of the dial position from the user injecting a shot. This is detectable by the microcontroller via the dosage sensor as well, since injections into the user should end with the dial returned to the initial, or home position, whereas adjustments of the knob to modify the dosage typically occur when the knob is set at a larger dosage and do not terminate in the initial, or home position of the knob. This is also detectable by the momentary switch, which is depressed for injections only, and not dosage adjustments. The data management unit may remind the user to hold drug delivery pen vertically when priming, if they are not doing so. In addition, if the user skips the priming step altogether, this will be apparent from the information collected by the microprocessor and accelerometer of the pen, and a visual or auditory warning, reminder, and/or instructions may be given to the user by the pen or the data management unit.

The inertial sensor is also utilized to determine if the user is performing the proper mixing technique before injecting insulin, another source of error in using drug delivery pen. Some insulin types must be mixed prior to use, such as 70/30 pre-mixed insulin. Mixing typically involves moving drug delivery pen from straight up to straight down ten times, an action that is easily detectable by an inertial sensor (located on or in the pen housing). A message may be displayed on the data management unit to remind the patient how to mix their insulin if they are using insulin that requires mixing prior to use. As used herein, the term "inertial sensor" is a sensor in which the gravitational effect of the earth can be accounted for so that the orientation of the inertial sensor relative to the earth can be determined. Likewise, the term "acceleration sensor" is intended to include an accelerometer or a 3-axis accelerometer where such acceleration sensor can be used to determine the orientation of the sensor relative to the earth.

In some cases, the DMU may ask the user to confirm whether a dose was a prime or an injection. In an embodiment, the inertial sensor can also be used to wake up the device if it is in sleep mode when the device is picked up by the user. In the dosing history menu on the glucose meter (not shown), it is possible for the user to toggle entries between prime and injection. As an example, the meter can display primes by indicating with the symbol "*" (for example) which injections were preceded by a prime. Applicant believes that this allows the displaying of as much information as possible on one screen on the meter without confusing the user by showing all the primes and injection doses together in one list.

The pens described herein incorporate electronics and use batteries to provide power. Applicants believe that the batteries need to be as small as possible so that the pen can be relatively small so that it is not intimidating to the patient, has easy portability, and can be used discretely. However, if the batteries are too small, they will need to be changed frequently, which is annoying to the user and in some cases can result in mis-dosing. Thus, it is useful to use low power electronics (note that low power MEMS inertial sensors are available) and to have the electronics go into "sleep" mode when the device is not in use in order to conserve power. An inertial sensor, activation switch or a resistive switch on the pen housing, or a microswitch in the pen cap can be used to wake the pen up from sleep mode. The inertial sensor can detect when the pen is picked up and/or handled and can trigger the electronics to wake up. Using this method, the display can be turned on immediately when the pen is picked up, and the user does not have to wait for the dosing dial to be turned.

After dialing in the desired dose, the injection is performed by inserting the needle into the skin and (with the user's thumb) fully depressing the knob. Once the knob is fully depressed, it must be held down for a predetermined period of time for the selected dosage to be fully injected. As provided herein, the momentary switch and processor would be able to determine the dosage injection event and duration thereof. Thereafter, the pen records such an event and the duration of the event into its memory. The user may perform this sequence until the cartridge is depleted. Assuming that the pen is a reusable pen, the empty drug cartridge could be thrown away and replaced with a new cartridge attached to the actuation portion of the reusable pen.

While some features have been described, other variations of the exemplary embodiments may be utilized in various combinations. For example, instead of a potentiometer, the pen may use an encoder to measure angular position and rotation of dosage selector. A switch may be used with the encoder to detect when the user presses on dosage actuation button of the pen to inject a drug, such as, for example, insulin, and allows for differentiation between dosage adjustments and injections. Such switch also detects how long the user continues to press on the dosage actuation button after injecting an insulin shot, as described earlier. In another example, when the switch is activated and after the encoder determines that dosage selector dial has returned to the zero position, the pen may communicate this information to the data management unit to initiate a timer on the meter that counts down the period of time that the user should keep the dial depressed. If the user releases pressure on the switch prematurely, a warning may be announced or displayed on the data management unit. Alternatively or in addition, a small display or LEDs on the pen may be used to cue the user as to how long to press on the dial. It is noted, however, that a display is not absolutely necessary—the device could just track the time that the knob is depressed and display a message/warning on the meter if the user does not hold down the button for a sufficient amount of time. The switch may also be configured to work with sensors other than encoders, for example the linear potentiometer. For example, the pen can: alert the user if they have not primed drug delivery pen using the inertial sensor; alert the user if a mixing step has not been performed (applicable to mixed insulins) using the inertial sensor; warn the user if the injection is incomplete (i.e., knob is not pressed all the way to zero); provide a timer that reminds the user to hold the knob down for several seconds during an injection; keep track of remaining insulin in drug delivery pen; remind user when it is time to inject; alert the user if injections have been missed or duplicated; alert the user if insulin is about to expire.

Several features may be utilized to reduce inaccuracies in the use of insulin pens. These include missing injections, duplicating injections, and improper priming. Improper priming is especially problematic if a needle (not shown) was left on between doses, allowing air to enter the drug cartridge. Some insulins, such as 70/30 pre-mix, must be mixed prior to injection. Neglecting to mix or improperly mixing 70/30 pre-mix before injection is a source of inaccuracy. The knob should be held for approximately 6 seconds during an injection to ensure the entire dose enters the body. Not holding the knob down long enough results in a partial dose. The pen can alert the user to these inaccuracies and thus helps to reduce them.

As mentioned previously, the dosage sensor of the pen may be used to measure insulin doses and transfer that information to a data management unit, which may be a glucose meter or a suitable data communication unit such as a mobile phone, mobile computer. The information that is transferred from the pen to the data management unit may be used to help master the use of drug delivery pen. Large potential sources of inaccuracy in the use of drug delivery pen are missed doses and double doses. However, the pens, as embodied herein, may help eliminate these sources of error by reminding the user of their dosing history. The complete dosing history (including doses and time and date the doses were delivered) may be made available to the user by selecting this option from the data management unit's menu. In addition, by having the most recent dosing information (time and amount) on a meter's display when the data management unit turns on, the user will immediately see if they have forgotten an injection every time they take a blood glucose measurement. In the same way that a data management unit may be used to alert a user when it's time to test blood glucose, the data management unit may also alert the user when to take insulin, or if an insulin injection has been missed. This information may also be displayed when the data management unit turns on.

Another source of error related to priming is that of neglecting to remove and dispose of needles after each injection. The meter, in one embodiment, would provide a display to generate a reminder stating that the needle should be removed with every use. Alternatively, the speaker mounted in or on the pen, which can be utilized to prompt the user with tones or prestored phrases configured for specific geographical areas (e.g., German for pens distributed in Germany, French for pens distributed in France and so on). Additionally, the speaker in the pen may be configured to allow a user to locate a misplaced one. Specifically, the pen may respond to an inquiry signal from a data management unit (or any electronic devices paired to the pen) to cause the speaker in the pen to emit tones or beeps in the event that it has been misplaced. This method also can be used to confirm that a particular pen is paired with a particular data management unit such as a glucose meter.

When injecting insulin with drug delivery pen, it is important to hold down on the knob with needle inserted for approximately six seconds, to ensure that the entire dose is delivered below the skin. The optimal amount of time is usually spelled out in drug delivery pen user's manual. A message may be displayed on either or both of the pen or the data management unit, reminding the user of proper technique if they are releasing the knob prematurely. The data management unit or the pen may display a countdown timer or emit a count down tone or signals, initiated when the knob is first pressed, letting the user know when they should release it.

Other pen-related usage reminders, such as the amount of time a pen may be used after removed from refrigeration, also may be incorporated into the smart pen and displayed on the data management unit as an aide to the user. To track the time a particular pen has been in use, the user would need to indicate the initiation of a new pen on the meter. In such embodiment, a switch is provided proximate the cartridge holder of the smart pen that is activated when a fresh cartridge is attached, signaling the initiation of a recharged pen. The user may be asked to confirm on the meter when a new pen is initiated by pressing a button and possibly entering some information, such as the amount of insulin in the new cartridge.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A drug delivery pen for confirming a dosage delivery protocol, the pen comprising:
   a pen housing that extends from a first end to a second end along a longitudinal axis, the housing being coupled to a drug cartridge disposed proximate the first end, the drug cartridge including a volume of one or more drugs disposed therein;
   a microprocessor disposed in the housing and operatively connected to a power source and a memory; and
   an inertial sensor connected to the housing and in electronic communication with the microprocessor, wherein the microprocessor confirms the dosage delivery protocol from output signals of the inertial sensor by:
      determining whether the housing has been shaken back and forth a predetermined number of times along the longitudinal axis to mix the one or more drugs disposed in the cartridge; and
      determining whether the pen housing, including the cartridge, has been oriented topmost and generally vertically with respect to a ground during a priming operation, wherein the microprocessor distinguishes whether the pen has delivered a priming shot or a dosage of the one or more drugs.

2. A drug delivery pen for confirming a dosage delivery protocol, the pen comprising:
   a pen housing that extends from a first end to a second end along a longitudinal axis, the housing being coupled to a drug cartridge disposed proximate the first end, the drug cartridge including a volume of one or more drugs disposed therein;
   a plunger rod having a portion disposed in the housing and at least a portion of the plunger rod coupled to the drug cartridge;
   a dosage selector mounted to the housing and coupled to the plunger rod;
   a microprocessor disposed in the housing and operatively connected to a power source and a memory;
   a momentary switch coupled to the plunger rod and electrically connected to the microprocessor so that actuation of the plunger rod to deliver drug causes the switch to be actuated and allows the microprocessor to detect actuation of the plunger rod; and
   an acceleration sensor connected to the housing and in electronic communication with the microprocessor, wherein the microprocessor confirms the dosage delivery protocol from output signals of the acceleration sensor by:
      determining whether the housing has been shaken back and forth a predetermined number of times along the longitudinal axis to mix the one or more drugs disposed in the cartridge; and
      determining whether the pen housing, including the cartridge, has been oriented topmost and generally vertically with respect to a ground during a priming operation, wherein the microprocessor distinguishes whether the pen has delivered a priming shot or a dosage of the one or more drugs.

3. The drug delivery pen of one of claim 1 or claim 2, in which the drug cartridge contains a drug selected from a group consisting of long acting insulin, rapid acting insulin, long and rapid acting mixed insulin, neutral protamine Hagedorn (NPH), growth hormone, glucagon-like peptide (GLP-1) analogs, pramlintide, or combinations thereof.

4. The drug delivery pen of claim 1, further comprising:
   at least a portion of a plunger rod coupled to the drug cartridge; and
   a dosage selector coupled to the plunger rod.

5. The drug delivery pen of one of claim 1 or claim 2, further comprising a transceiver disposed in the housing and coupled to the microprocessor to transmit and receive data relating to dosage delivery of a drug dosage in the drug cartridge to a data management unit remote from the drug delivery pen.

6. The drug delivery pen of one of claim 1 or claim 2, further comprising a dosage indicator display provided on the pen housing, the dosage indicator display providing a representation of dosage selected by a user of the drug delivery pen.

7. The drug delivery pen of one of claim 1 or claim 2, further comprising a Radio-Frequency-Identification tag coupled to the drug cartridge and configured to store information selected from a group including type of drug(s) in the cartridge, volume of drug in the cartridge, expiration date, batch date, lot number, manufacturer identification or combinations thereof.

8. The drug delivery pen of claim 2, further comprising a dosage sensor attached to the dosage selector of the pen and coupled to the microprocessor so as to provide dosage delivery data upon displacement of the dosage selector.

9. A diabetes management system comprising:
   a data management unit including:
      a memory;
      a processor coupled to the memory;
      a display coupled to the processor; and
      a transceiver to receive and transmit data; and
   a drug delivery pen for confirming a dosage delivery protocol, the pen comprising:
      a pen housing that extends from a first end to a second end along a longitudinal axis, the housing being coupled to a drug cartridge disposed proximate the first end, the pen housing having a dosage indicator window and a dosage selector coupled to the plunger rod;
      a memory;
      a microprocessor coupled to the memory of the pen; and
      an inertial sensor connected to the housing and in electronic communication with the microprocessor, wherein the microprocessor confirms the dosage delivery protocol from output signals of the inertial sensor by:
         determining whether the housing has been shaken back and forth a predetermined number of times along the longitudinal axis to mix the one or more drugs disposed in the cartridge; and determining whether the pen housing, including the cartridge, has been oriented topmost and generally vertically with respect to a ground during a priming operation, wherein the microprocessor distinguishes whether the pen has delivered a priming shot or a dosage of the one or more drugs.

10. The system of claim 9, further comprising a dosage sensor attached to the dosage selector of the pen and coupled to the processor so as to provide data upon displacement of the dosage selector.

11. The system of claim 10, wherein the transceiver transmits and receives data relating to dosage delivery of a drug dosage in the drug cartridge to the data management unit.

12. The system of claim 9, in which the drug cartridge contains a drug selected from a group consisting essentially of long acting insulin, rapid acting insulin, long and rapid acting mixed insulin, neutral protamine Hagedorn (NPH), growth hormone, glucagon-like peptide (GLP-1) analogs, pramlintide, or combinations thereof.

13. The system of claim 9, in which the data management unit further comprises an analyte sensor coupled to the processor to provide signals indicative of analyte value in a user's biological fluid.

14. The system of claim 9, in which the data management unit comprises a mobile phone.

15. The system of claim 9, in which the data management unit comprises a mobile computer.

16. The system of claim 9, in which the data management unit comprises a network server located at a remote location from the communication module.

17. The system of claim 9, further comprising a radio-frequency-identification (RFID) tag being coupled to the drug cartridge to store data selected from a group including a type of drug(s) in the cartridge, volume of drug in the cartridge, expiration date, batch date, lot number, manufacturer identification or combinations thereof.

18. The system of claim 17, further comprising a radio-frequency-identification tag (RFID) reader disposed on one of the pen and the data management unit to interrogate the RFID tag for transfer of the information stored on the RFID tag.

19. A diabetes management system comprising:
a data management unit including:
　a memory;
　a processor coupled to the memory;
　a display coupled to the processor; and
　a transceiver to receive and transmit data;
　a radio-frequency-identification reader; and
a drug delivery pen comprising:
　a pen housing that extends from a first end to a second end along a longitudinal axis, the housing being coupled to a drug cartridge disposed proximate the first end, the pen housing having a dosage indicator window and a dosage selector coupled to the plunger rod;
　a memory;
　a microprocessor coupled to the memory of the pen;
　a radio-frequency-identification tag attached to the drug cartridge and configured to store data selected from a group including a type of drug(s) in the cartridge, volume of drug in the cartridge, expiration date, batch date, lot number, manufacturer identification or combinations thereof; and
an inertial sensor connected to the housing and in electronic communication with the microprocessor, wherein the microprocessor confirms the dosage delivery protocol from output signals of the inertial sensor by:
　determining whether the housing has been shaken back and forth a predetermined number of times along the longitudinal axis to mix the one or more drugs disposed in the cartridge; and
　determining whether the pen housing, including the cartridge, has been oriented topmost and generally vertically with respect to a ground during a priming operation, wherein the microprocessor distinguishes whether the pen has delivered a priming shot or a dosage of the one or more drugs.

* * * * *